US011191926B2

(12) United States Patent
Chang et al.

(10) Patent No.: US 11,191,926 B2
(45) Date of Patent: *Dec. 7, 2021

(54) CATHETER FIXING BAND

(71) Applicant: SUNGSHIN WOMEN'S UNIVERSITY INDUSTRY—ACADEMIC COOPERATION FOUNDATION, Seoul (KR)

(72) Inventors: HaeJin Chang, Seoul (KR); ChanJu Park, Seoul (KR); InHye Park, Gwangmyeong-si (KR); JooYeon Jung, Seoul (KR); MiHyun Kim, Suwon-si (KR)

(73) Assignee: SUNGSHIN WOMEN'S UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 258 days.

This patent is subject to a terminal disclaimer.

(21) Appl. No.: 16/555,338

(22) Filed: Aug. 29, 2019

(65) Prior Publication Data

US 2019/0381280 A1 Dec. 19, 2019

Related U.S. Application Data

(63) Continuation of application No. 14/935,776, filed on Nov. 9, 2015, now Pat. No. 10,441,751.

(30) Foreign Application Priority Data

Sep. 30, 2015 (KR) .......................... 10-2015-0137372
Oct. 30, 2015 (KR) .......................... 10-2015-0151667

(51) Int. Cl.
*A61M 25/02* (2006.01)

(52) U.S. Cl.
CPC ....... *A61M 25/02* (2013.01); *A61M 2025/026* (2013.01); *A61M 2025/0206* (2013.01);
(Continued)

(58) Field of Classification Search
CPC .......... A61M 25/02; A61M 2025/0246; A61M 2025/0206; A61M 2025/026; A61M 2025/0213
See application file for complete search history.

(56) References Cited

U.S. PATENT DOCUMENTS 4,397,647 A  8/1983 Gordon
5,403,285 A  4/1995 Roberts
(Continued)

*Primary Examiner* — Tarla R Patel
(74) *Attorney, Agent, or Firm* — Hauptman Ham, LLP

(57) ABSTRACT

Provided is a catheter fixing band for fixing a tube bent and connected to a catheter to the catheter fixing band, according to the present disclosure, a catheter fixing band includes: a body detachably fixed to a human body and having a catheter hole open to expose a portion of the human body; and a cover unit detachably attached to the body to open or close the catheter hole, in which the cover unit includes a fixing member fixing the catheter to a predetermined position of the cover unit, and has a shape forming integral concept in relation to flow of fluid in the catheter when the cover unit covers the catheter hole and the catheter is fixed to the fixing member.

1 Claim, 23 Drawing Sheets

(52) U.S. Cl.
CPC ............... *A61M 2025/0213* (2013.01); *A61M 2025/0246* (2013.01)

(56) References Cited

U.S. PATENT DOCUMENTS

| | | | |
|---|---|---|---|
| 6,322,539 B1 | 11/2001 | Cook | |
| 6,540,724 B1 | 4/2003 | Harris | |
| 7,988,673 B2 | 8/2011 | Wright et al. | |
| 8,632,492 B2 | 1/2014 | Delegge | |
| 10,441,751 B2 * | 10/2019 | Chang | A61M 25/02 |
| 2002/0174872 A1 | 11/2002 | Cyphers et al. | |
| 2005/0054985 A1 | 3/2005 | Mogg | |
| 2010/0217201 A1 | 8/2010 | Lee et al. | |

* cited by examiner

CATHETER FIXING BAND

CROSS-REFERENCE TO RELATED APPLICATIONS

The present application is a Continuation of U.S. application Ser. No. 14/935,776, filed on Nov. 9, 2015, which claims the priorities of Korean Patent Application No. 10-2015-0137372, filed on Sep. 30, 2015, and Korean Patent Application No. 10-2015-0151667, filed on Oct. 30, 2015, in the Korean Intellectual Property Office, the disclosure of which is incorporated herein by reference.

BACKGROUND

Technical Field

The present disclosure relates to a catheter fixing band and, more particularly, to catheter fixing band that can fix a tube, which is bent and connected to a catheter, to the catheter fixing band.

Description of the Related Art

In general, a catheter is a tool that is inserted into a portion of the body of a patient to measure waste matters, dialyze blood, or inject medicine.

When a catheter is inserted in the body of a patient, medicine is injected into the body through a tube connected to the catheter or waste matters are discharged out of the body through the tube. In this case, in order to fix the inserted catheter, generally, an adhesive bandage is used to attach the catheter to the skin of the patient after the catheter is inserted in a portion of the body.

However, when a catheter is fixed by an adhesive bandage, as in the related art, the catheter is attached directly to the body of a patient. In this case, the catheter is moved and the catheter-inserted portion is hurt, so secondary infection is caused by permeation of bacteria through the injury.

Further, in order to adjust the tube connected to the catheter, it is required to take off the adhesive bandage, adjust the fixing member, and attach the catheter back to the body, so the needle of the catheter is moved inside the skin of the patient or it is required to insert the needle of the catheter back into the body of the patient, so the patient may feel painful.

On the other hand, in order to suppress the needle at the end of a catheter is moved inside the skin of a patient by the tube connected to the catheter and moved by being touched with external objects, the tube is generally bent in a U-shape and then fixed to the skin of a patient. However, it may be difficult even in this case to sufficiently suppress movement of the tube due to a touch with external objects.

Accordingly, there is an increasing need for a catheter fixing band that can reduce movement even if a tube connected to a catheter is moved by a touch with external objects and that can fix the catheter and the tube.

SUMMARY

The present disclosure has been made in an effort to solve the problems and intended to provide a catheter fixing band that can reduce movement of a catheter inserted in a patient.

Further, the present disclosure provides a catheter fixing band that reduces pain that may be applied to a patient because a need for using an adhesive bandage to adjust a tube connected to a catheter is reduced.

Further, the present disclosure provides a catheter fixing band that reduces the contact portion between a tube connected to a catheter and an external object and reduces movement of the tube connected to the catheter.

It should be noted that objects of the present disclosure are not limited to the above-mentioned object and other objects of the present disclosure will be apparent to those skilled in the art from the following descriptions.

In order to achieve the above-described object, an aspect of the present disclosure provides a catheter fixing band including: a body detachably fixed to a human body and having a catheter hole open to expose a portion of the human body; and a cover unit detachably attached to the body to open or close the catheter hole, in which the cover unit includes a fixing member fixing the catheter to a predetermined position of the cover unit, and has a shape forming integral concept in relation to flow of fluid in the catheter when the cover unit covers the catheter hole and the catheter is fixed to the fixing member.

According to another feature of the present disclosure, the body has holes at both ends to pass a portion of a human body.

According to yet another feature of the present disclosure, the body has a coupling member elongated and coupled back to the body after winding around a portion of a human body.

According to still another feature of the present disclosure, the cover unit is at least connected to the body and covers the catheter hole.

According to still another feature of the present disclosure, the cover unit has a shape bringing up the image of an elephant, and the fixing member is disposed inside the nose of the elephant shape and fixes the catheter or the tube connected to the catheter to the cover unit by covering the catheter or the tube.

According to still another feature of the present disclosure, the fixing member has Velcro tape portions extending to both sides from the nose of the elephant shape and covering the catheter or the tube.

According to still another feature of the present disclosure, the cover unit has a shape bringing up the image of a lion, and the fixing member is disposed inside the mouth or the mane of the lion and fixes the catheter or the tube connected to the catheter to the cover unit by covering the catheter or the tube.

According to still another feature of the present disclosure, the cover unit has a tube support portion extending in a U-shape from an end to cover the tube connected to the catheter and make the tube bend in a U-shape.

According to still another feature of the present disclosure, the tube support portion has a cover semicircle formed in the shape of a semicircle and made of a rigid material not to be moved by a predetermined level of or less force.

According to still another feature of the present disclosure, the tube support portion has a grip curved surface extending around the cover semicircle, being made of an elastic material so that the tube is inserted and seated in the cover semicircle, and supporting the tube.

According to still another feature of the present disclosure, splint supporting a contact portion in contact with the body of a patient is disposed on the body.

According to still another feature of the present disclosure, the body includes: a cover fixed adjacent to the catheter hole, covering the catheter hole, and detachably attached to the body; and a catheter fixing member disposed on the body and fixing the catheter or the tube connected to the catheter to the body.

According to still another feature of the present disclosure, the catheter fixing member includes a first fixing member disposed at a side of the catheter hole, covering the tube to fix the tube coming out of the catheter hole to the body, and detachably attached to the body.

According to still another feature of the present disclosure, the catheter fixing member includes a second fixing member having an end detachably attached to the cover so that the tube connected to the catheter is fixed to the cover after bending.

According to still another feature of the present disclosure, a velcro tape portions are disposed at both ends of the body so that the body covers the body of a patient, and the velcro tape portions are elongated and wound around the body of the patient, thereby fixing the body on the body of the patient.

According to still another feature of the present disclosure, a finger hole through which some of fingers of a patient is formed at a side of the body, and a body over the finger hole can be bent after fingers of the patient are inserted.

According to still another feature of the present disclosure, the velcro tape portions include a first velcro tape portion disposed close to the finger hole and a second velcro tape portion disposed opposite to the first velcro tape portion, and the first velcro tape portion is folded to cover the fixing member fixing a catheter, after a portion of the body is folded by the finger hole.

According to still another feature of the present disclosure, the body has an attachment side that is directly attached to the skin of a patient.

According to the catheter fixing band of the present disclosure, since the cover unit not only cover the catheter hole and fixes the tube connected to the catheter, but makes integral concept in relation to flow of fluid in the catheter, so it is possible to give mental stability of a patient.

Further, according to the catheter fixing band of the present disclosure, since the cover unit can be smoothly bent in a U-shape by the cover unit that covers the tube connected to the catheter and bends the tube in a U-shape, there is no need for another component for curving the tube.

Further, according to the catheter fixing band of the present disclosure, since the cover semicircle, where the tube bending in a U-shape is inserted, is made of a rigid material that is not moved under a predetermined level or less external force, it is possible to protect the tube against external force.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Figure 1A:
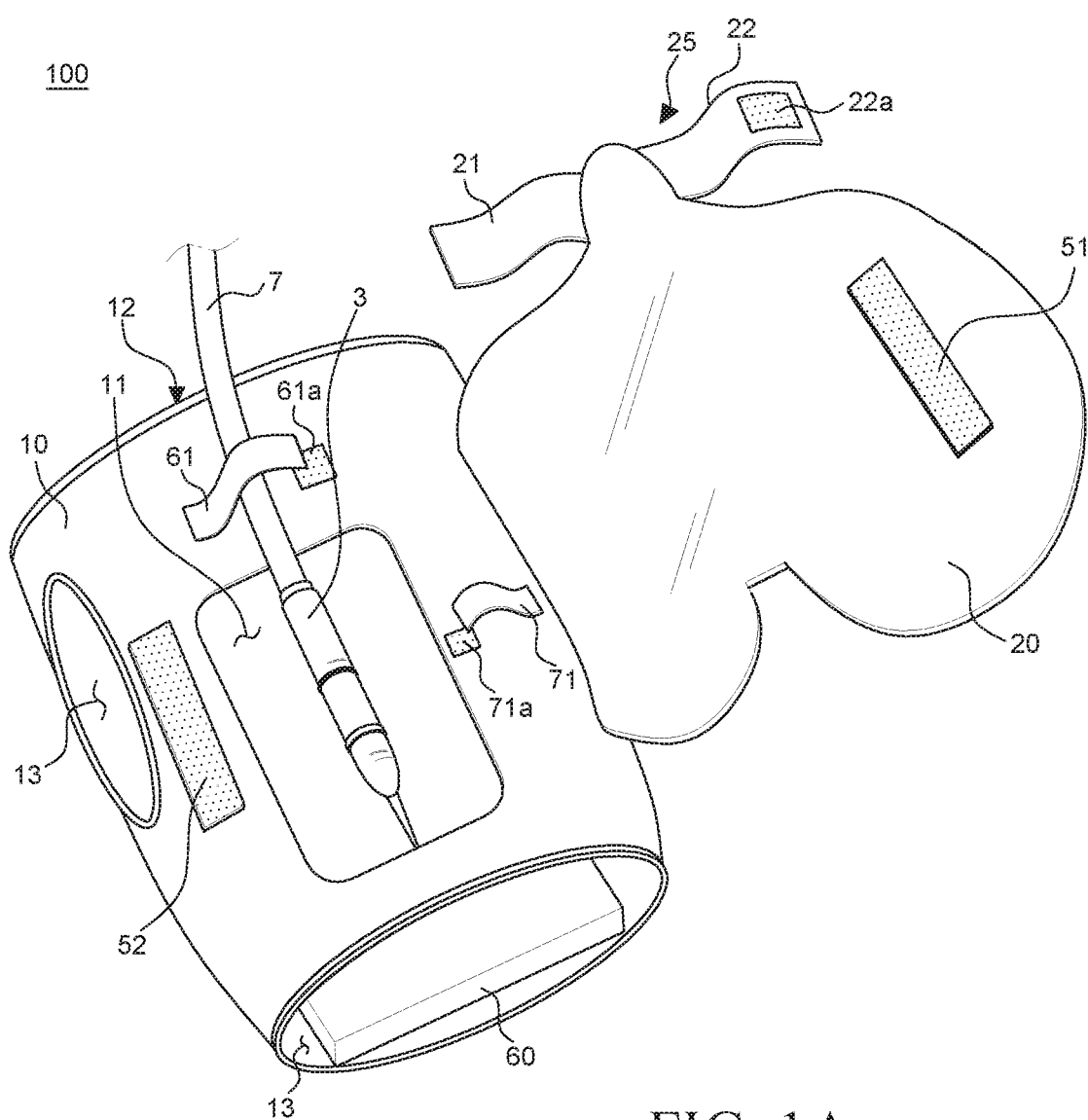
FIGS. 1a and 1b are perspective views illustrating a catheter fixing band according to an embodiment of the present disclosure.

Advantages and features of the present disclosure and methods for achieving them will become apparent from the descriptions of exemplary embodiments herein below with reference to the accompanying drawings. However, the present disclosure is not limited to exemplary embodiments disclosed herein but may be implemented in various different forms. The exemplary embodiments are provided for making the disclosure of the present disclosure thorough and for fully conveying the scope of the present disclosure to those skilled in the art. It is to be noted that the scope of the present disclosure is defined only by the claims.

As used herein, a phrase "an element A on an element B" refers to that the element A may be disposed directly on the element B and/or the element A may be disposed indirectly on the element B via another element C. Like reference numerals denote like elements throughout the descriptions.

Terms such as first, and second are used to distinguish arbitrarily between the elements such terms describe and these terms are not necessarily intended to indicate temporal or other prioritization of such elements. These terms are merely used for distinguishing one component from the other components. Accordingly, as used herein, a first element may be a second element within the technical scope of the present disclosure.

Figure 1B:
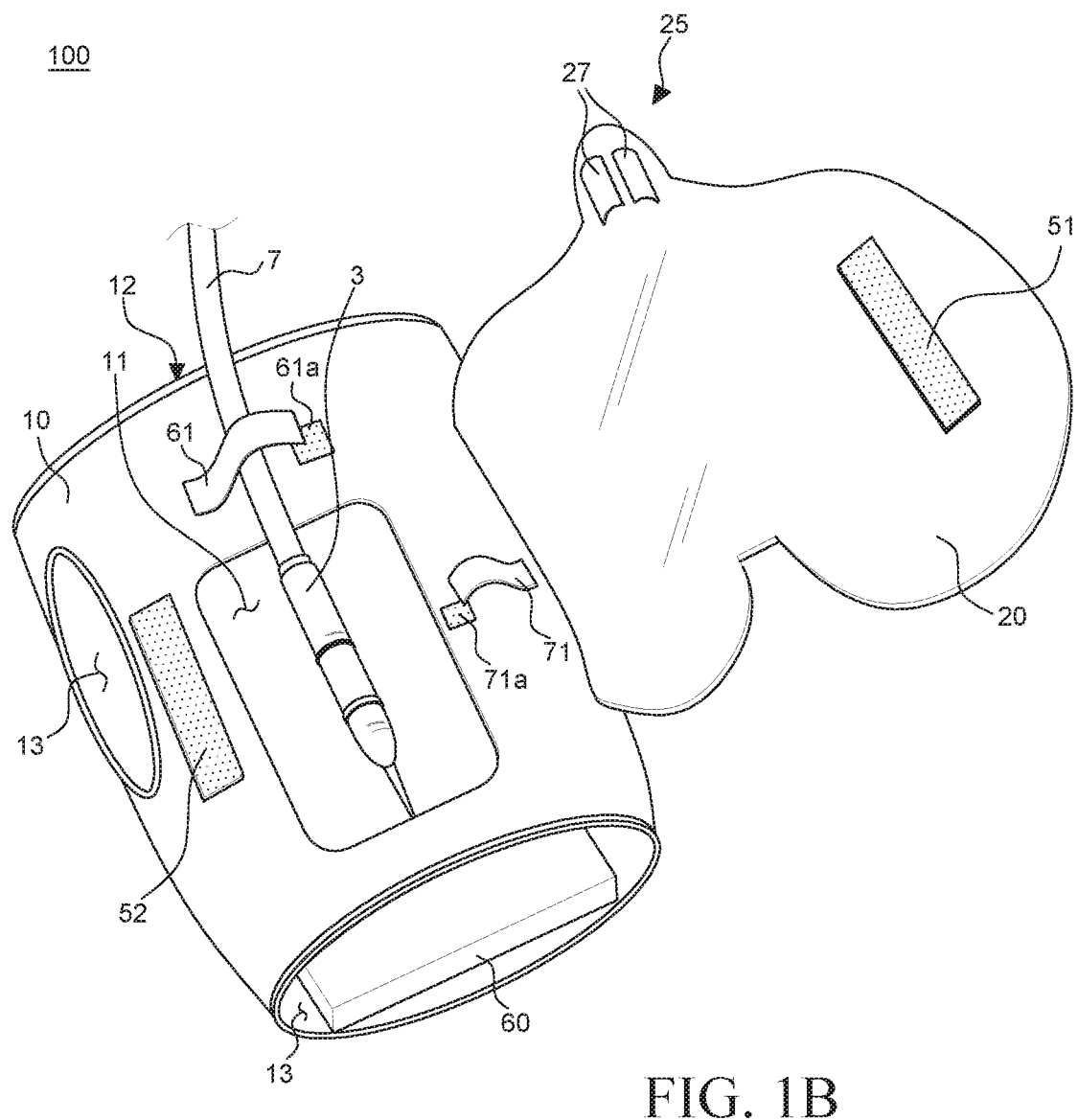
Figure 2:
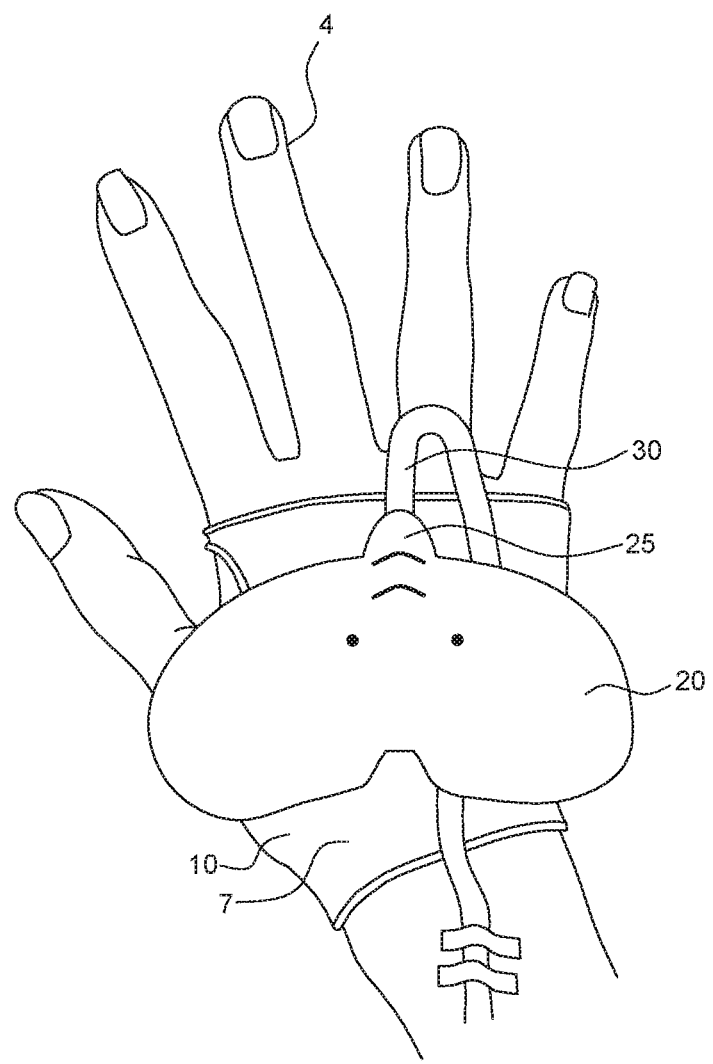
FIG. 2 is a perspective view illustrating that the catheter fixing band illustrated in FIG. 1a is worn on a hand of a patient.
Figure 3:
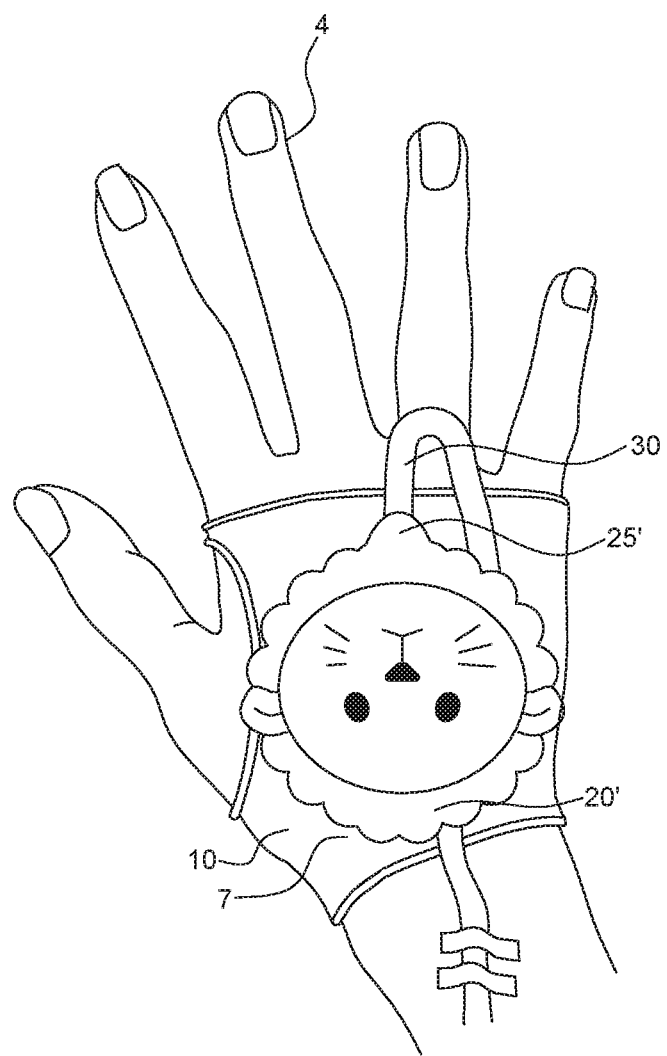
FIG. 3 is a perspective view illustrating that a catheter fixing band according to another embodiment of the present disclosure is worn on a hand of a patient.

FIGS. 1a and 1b are perspective views illustrating a catheter fixing band according to an embodiment of the present disclosure. FIG. 2 is a perspective view illustrating that the catheter fixing band illustrated in FIG. 1a is worn on a hand of a patient. FIG. 3 is a perspective view illustrating that a catheter fixing band according to another embodiment of the present disclosure is worn on a hand of a patient.

Referring to FIGS. 1a, 1b, and 2, a catheter fixing band 100 according to an embodiment of the present disclosure includes a body 10 and a cover unit 20.

The body 10 is detachably attached to a human body. The body 10 may be formed approximately in a cylindrical shape. The body 10 has holes 12 and 13 for inserting a hand, an arm, or a leg of a patient at both ends. A catheter hole 11 for exposing a portion of a body and inserting a catheter 3 is formed through a side of the body 10.

As described above, the holes 12 and 13 for inserting a hand of a patient is formed at both ends of the body 10. In the holes 12 and 13, the first hole 13 may cover a wrist and the other hole 12 may expose fingers, so the degrees of tightening are different and accordingly the sizes of the holes may be different. The holes 12 and 13 are made of an elastic material and tighten a hand or a wrist of a patient such that the body 10 can be brought in close contact with the hand of the patient.

A finger hole 13 for passing at least some of the fingers of a patient may be formed in the body 10. The finger hole 13 may be formed at a side of the body 10 to be adjacent to any one of the holes through which a hand of a patient can be inserted. In detail, referring to FIGS. 4 and 5, the finger hole 13 may be formed adjacent to the hole through which fingers are exposed, in the holes at both ends. It is possible to wear the catheter fixing band 100, like a glove having no space for fingers, with a thumb protruding through the finger hole 13.

Meanwhile, a splint 60 for supporting an arm of a patient in contact with it may be disposed on the other side of the body 10. The splint 60 suppresses a wrist of a patient from folding or supports an arm of a patient and can reduce the space between the body 10 and an arm of a patient such that the body 10 is further brought in contact with the arm of the patient. Unlike the figures, the splint 60 may be curved to be able to support and surround a wrist or an arm of a patient.

A side of the cover unit 20 may be fixed to a side of the catheter hole 11 with respect to the body 10. The cover unit 20 rotatably connected to the body 10 only at one side to open/cover the catheter hole 11.

The cover unit 20 has a fixing member 25 for fixing the catheter 3 at a predetermined position on the cover unit 20.

Referring to FIG. 1a, the fixing member 25 includes Velcro tape portions 21 and 22 extending to both sides from an elephant-shaped nose to cover a catheter or a tube. The first Velcro tape portion 21 and the second Velcro tape portion 22 cover a tube so that the tube is fixed to the elephant-shaped fixing member 25. A fixing member Velcro tape 22a on the inner side of the end portion of the second Velcro tape portion 22 sticks to the Velcro tape on the outer side of the first Velcro tape portion 21, so a tube can be covered and fixed. That is, the catheter 3 or the tube 7 connected to the catheter is covered with the fixing member 25 and connected to the fixing member 25 of the cover unit 20.

Meanwhile, referring to FIG. 1b, the fixing member 25 may have a tube fixing members 27 protruding at the elephant-shaped nose to cover a tube. The tube fixing member 27 may be formed in a cylindrical shape. Further, the tube fixing member 27 may be hard at a predetermined level so that a tube can be inserted and supported. The shape of the tube fixing member 27 may be similar to that of a grip 442 of a tube support portion 440 illustrated in FIG. 13.

When the cover unit 20 covers the catheter hole 11 and the catheter 3 is fixed to the fixing member 25, the tube 7 and the cover unit 20 make an integral concept in relation to the flow of fluid in the catheter 3. In detail, when the cover unit 20 covers the catheter hole 11, an integral concept in which fluid flows into or out of the end of the elephant-shaped nose.

The cover unit 20 has a shape bringing up the image of an elephant, and the fixing member 25 is disposed inside the nose of the elephant shape, so it covers the catheter 3 or the tube 7 connected to the catheter to fix them to the cover unit 20.

Velcro tapes 51 and 52 corresponding to each other may be disposed on the cover unit 20 and the body 10, respectively. In detail, Velcro tapes 51 and 52 corresponding to each other may be disposed at the portions where the cover unit 20 is turned to be in contact with the body 10. The cover unit 20 and the body 10 can be detachably attached to each other by the Velcro tapes 51 and 52.

Meanwhile, various pictures may be drawn on the cover unit 20. For example, as illustrated in the figures, an elephant may be drawn. Further, a tiger may be drawn on the cover unit 20 and the tube support portion 30 may be the tail of the tiger. Such pictures can reduce fear of the catheter 3 and give mental stability.

A first support member 61 and a second support member 71 for fixing and supporting the tube 7 coming out of the catheter hole 11 may be disposed on the body 10.

The first support member 61 is disposed at a side of the catheter hole 11. The side is in the direction in which the tube 7 connected to the catheter 3 extends. The first support member 61 can somewhat fix and attach the tube 7 to the body.

The second support member 71 is disposed at another side of the catheter hole 11. The second support member 71 may be disposed between the catheter hole 11 and the cover unit 20 or on the opposite side so that the tube 7 passing through the first support member 61 can be bent in a U-shape and then fixed. In the figures, the second support member 71 is disposed between the catheter hole 11 and the cover unit 20.

Since the second support member 71 covers the tube and then the cover unit 20 covers a portion of the body 10, so the tube 3, as illustrated in FIG. 2, is positioned under the cover unit 20. Accordingly, the area where the tube 3 is exposed to the outside decreases, so the tube 3 can be further protected.

The first support member 61 and the second support member 71 stick to a first support member Velcro tape 61a and a second support member Velcro tape 71b, respectively, thereby supporting the tube 7.

Referring to FIG. 3, a cover unit 20' has a shape bringing up the image of a lion. Further, a fixing member 25' is disposed inside the mouth or the mane of the lion shape and fixes the catheter 3 or the tube 7 connected to the catheter to the cover unit 20' by covering the catheter 3 or the tube 7 connected to the catheter.

Figure 4:
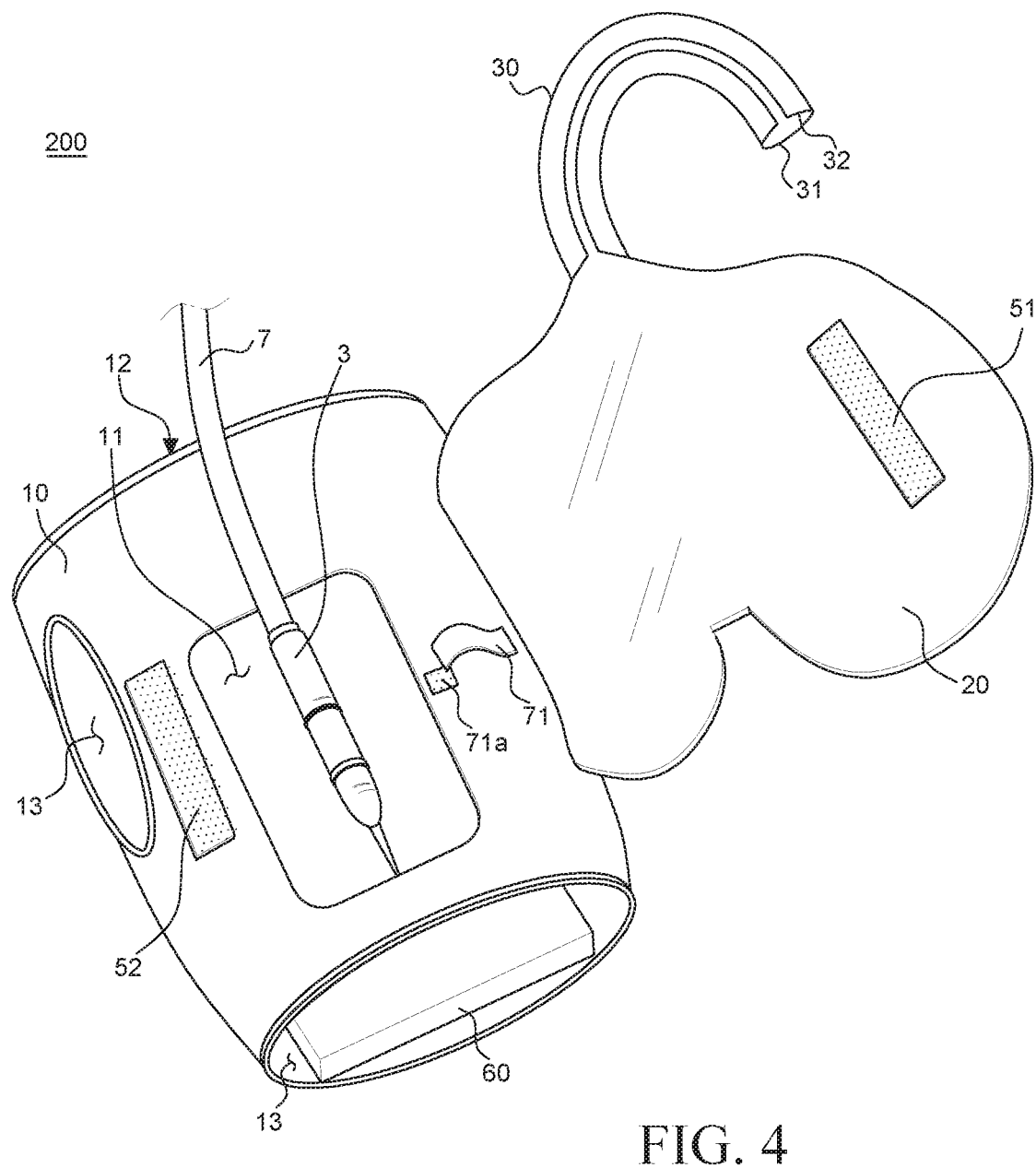
FIG. 4 is a perspective view illustrating a catheter fixing band according to another embodiment of the present disclosure.
Figure 5:
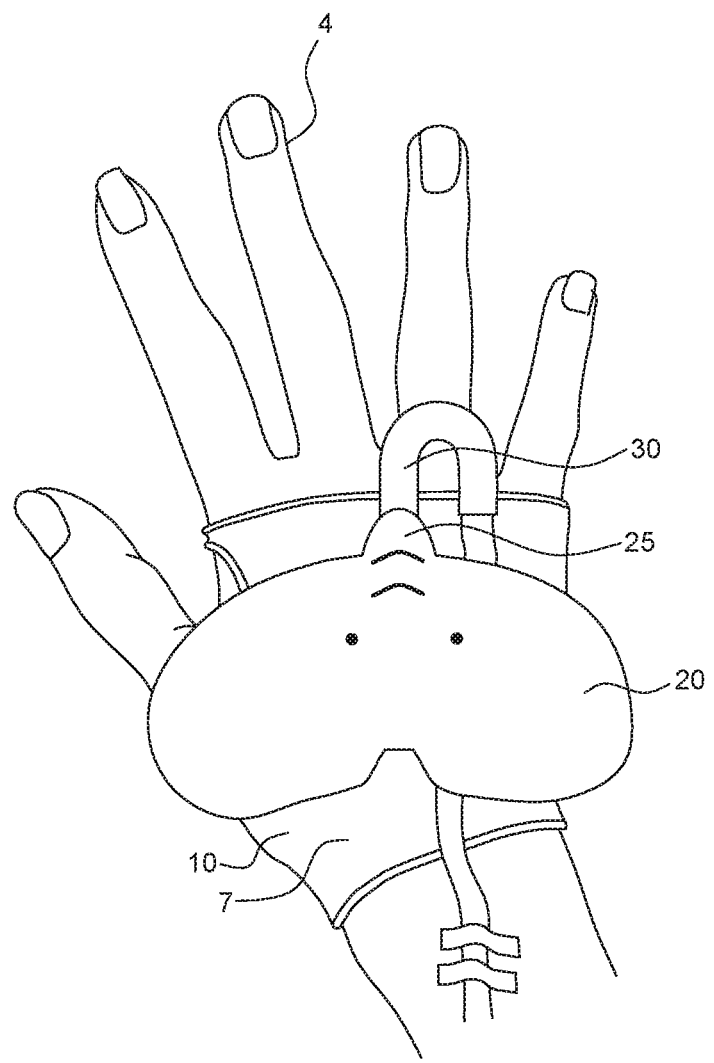
FIG. 5 is a perspective view illustrating that the catheter fixing band illustrated in FIG. 4 is worn on a hand of a patient.

FIG. 4 is a perspective view illustrating a catheter fixing band 200 according to another embodiment of the present disclosure. FIG. 5 is a perspective view illustrating that the catheter fixing band 200 illustrated in FIG. 4 is worn on a hand of a patient.

A catheter fixing band 200 according to another embodiment of the present disclosure is the same as or similar to the catheter fixing band 100 described with reference to FIGS. 1 and 2, except that a tube support portion 30 for covering and supporting a tube is added, so the same or similar configuration is not described here.

A cover unit 20 has a tube support portion 30 covering a tube 7 connected to a catheter 3 and extending from an end such that the tube 7 is bent in a U-shape.

The tube support portion 30 extends in a U-shape in a direction in which the tube 3 connected to the catheter 3 inserted in a patient comes out of a catheter hole 11. The tube support portion 30 may have a cover semicircle 31 and a grip curved surface 32.

The cover semicircle 31 may be formed in a semicircular shape and may be made of a rigid material not to move due to a predetermined external force. The tube 7 connected to the catheter 3 may be inserted into the cover semicircle 31. The cover semicircle 31 is made of a rigid material so that the tube 7 is not moved by an external force from the outside. The external force that cannot move the cover semicircle 31 is small such that the cover semicircle 31 is not moved even if a predetermined force is applied due to an external touch.

Meanwhile, unlike the figures, the tube support portion 30 may have a plurality of joints. The joints are not moved under a predetermined level of or less external force. Accordingly, even if external force is applied to the tube support portion 30, only the degree of bending of the joints is changed, but the force applied to the tube 7 is not large.

Figure 13:
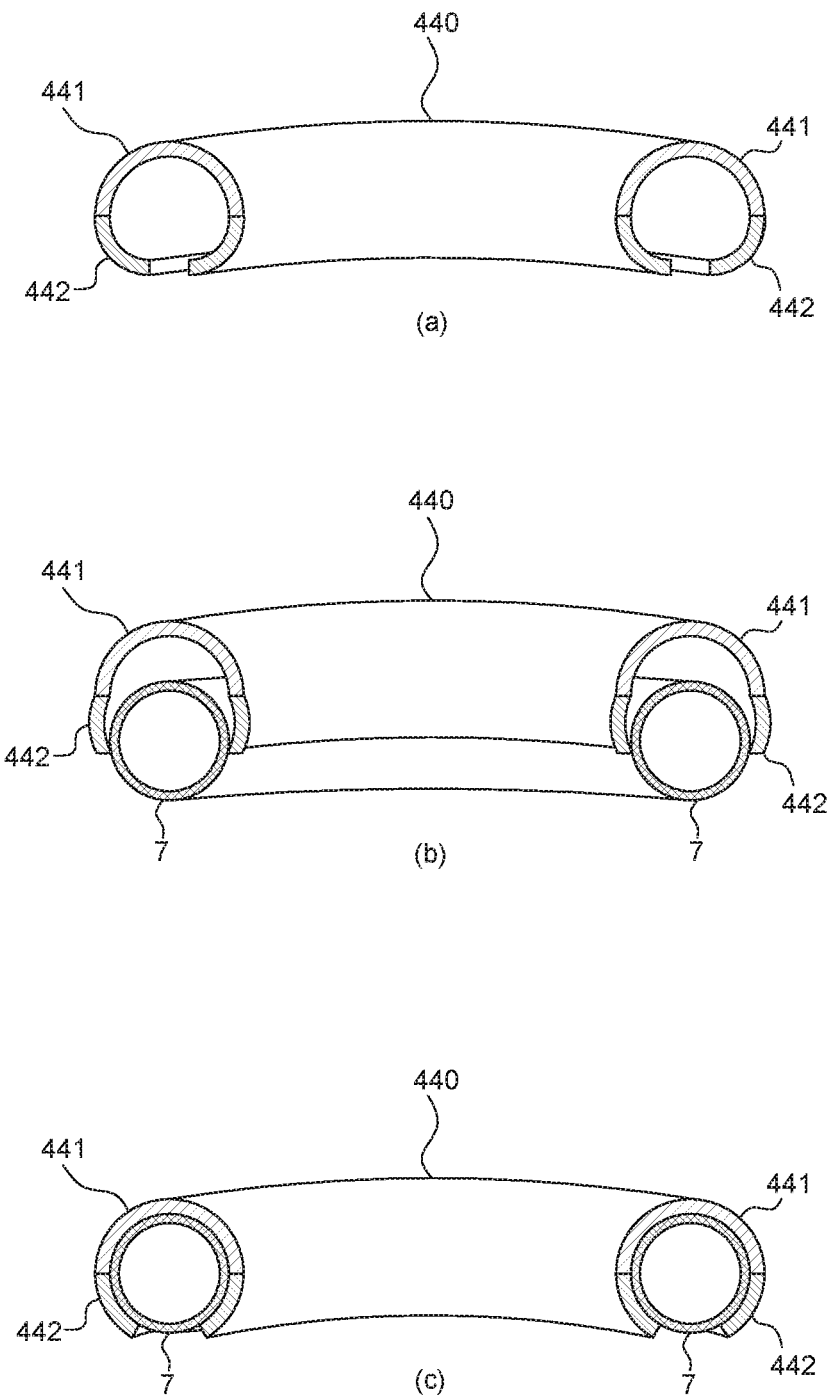
FIG. 13 is a cross-sectional view illustrating the cross-section taken along line A-A' of the cover unit illustrated in FIG. 12 and a process of inserting a tube into the cover unit.

The grip curved surface 32 extends around the cover semicircle 31. When the tube 7 is inserted in the cover semicircle, it may be made of an elastic material that can press the tube 7 to the cover semicircle 31 such that the tube 7 is seated in the cover semicircle 31. Referring to (a) of FIG. 13 illustrating in detail the tube support portion 30, the grip curved surface 342 extends around the cover semicircle 341. Further, referring to (b), tube 7 is being put into the tube support portion 340. Referring to (c), the tube 7 is seated inside the cover semicircle 341 and the grip curved surface 342 presses the tube 7 so that the tube 7 is seated inside the cover semicircle 341. This configuration will be described in detail below.

The tube 7 may be inserted and bent in a U-shape in the tube support portion 30 after passing through the catheter hole 11. Further, as described above, the tube 7 is inserted in the cover semicircle 31, so it can be protected from external force applied to the tube 7 by the cover semicircle 31. Since the tube 7 is protected by the cover semicircle 31, even if the tube 7 is moved, the catheter 3 connected to the tube 7 cannot be shaken in an arm of a patient. Accordingly, it is possible to reduce a pain applied to a patient due to shaking of a needle in an arm of the patient according to movement of the catheter 3.

Figure 6:
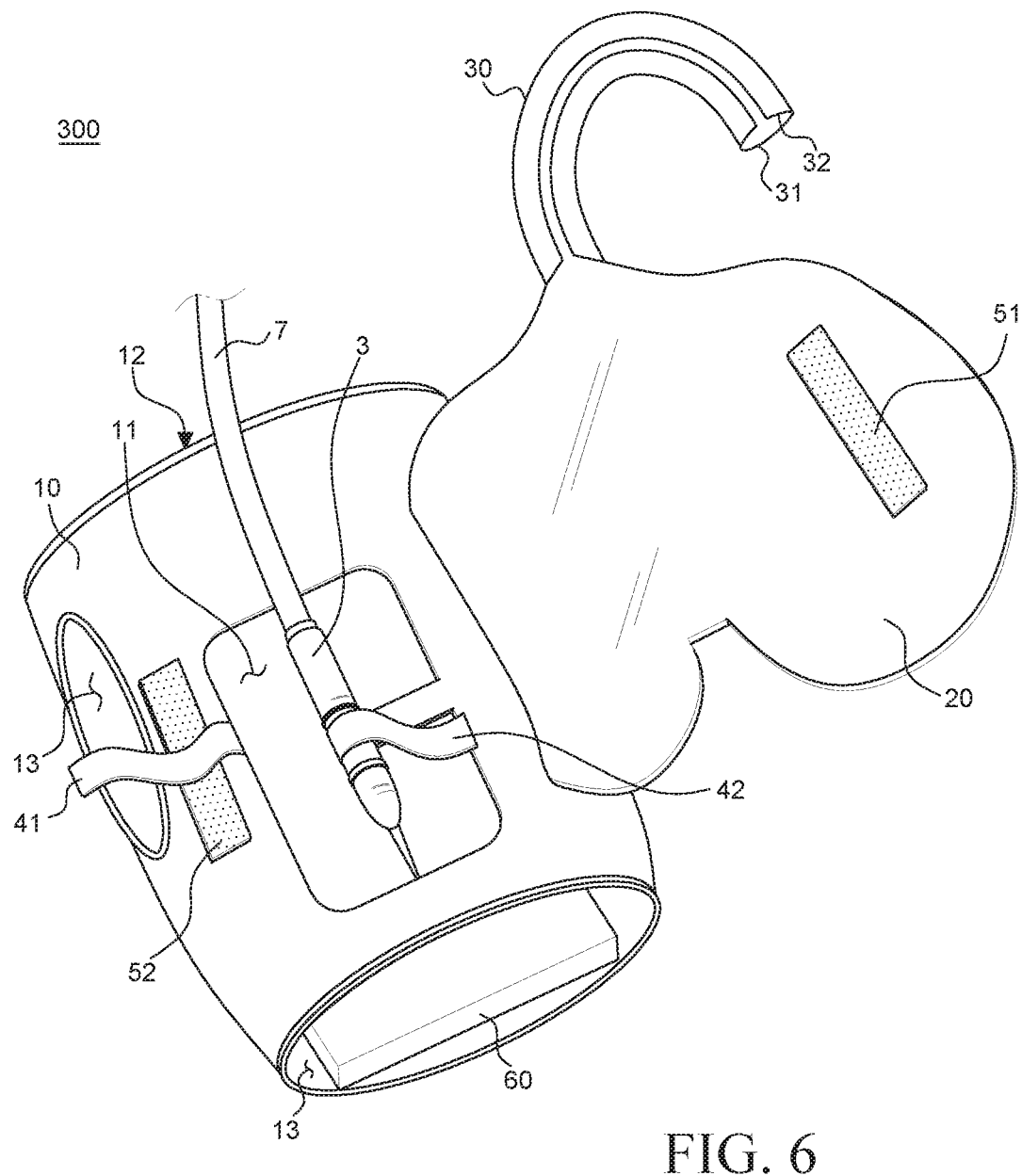
FIG. 6 is a perspective view illustrating a catheter fixing band according to another embodiment of the present disclosure.
Figure 7:
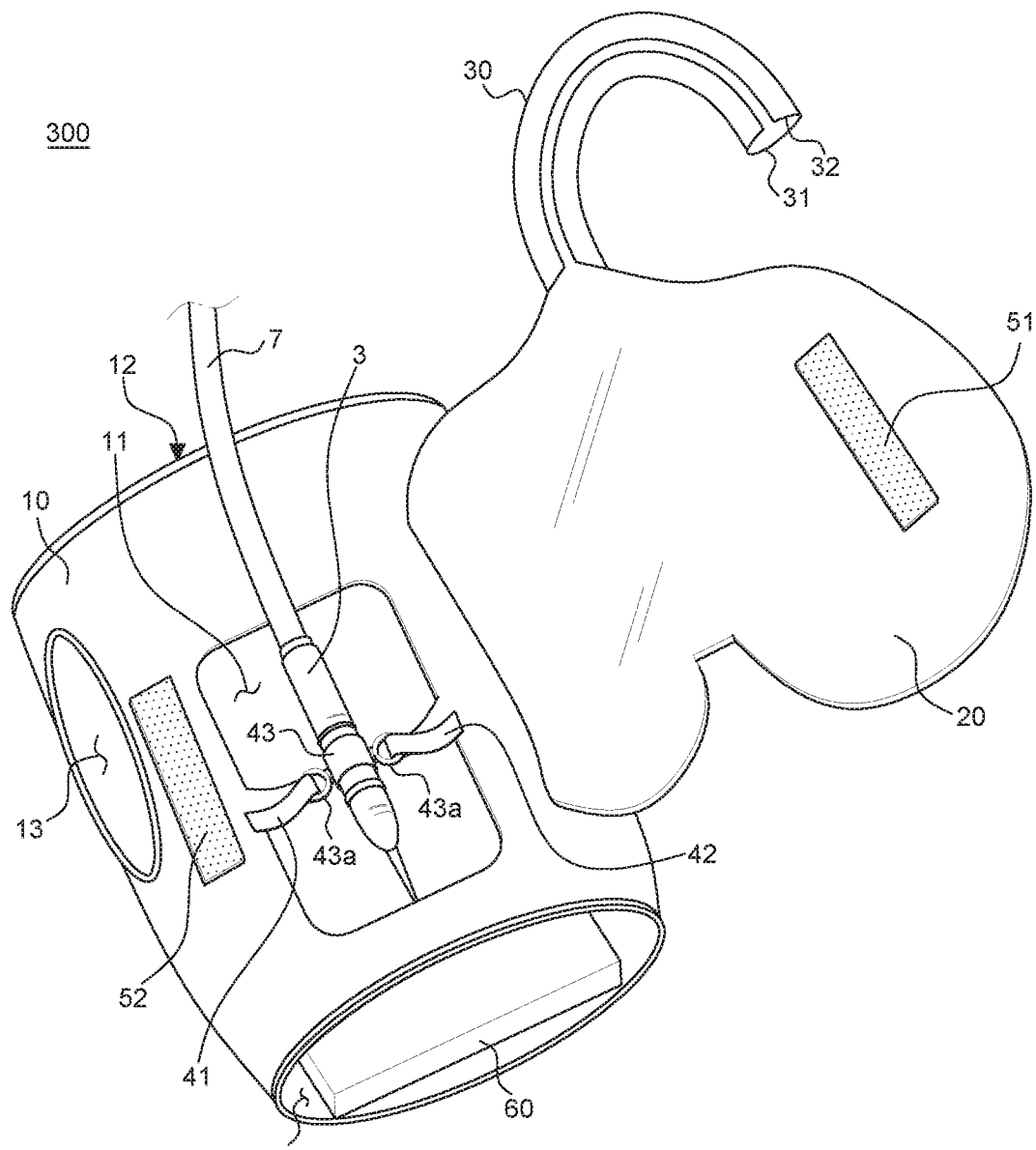
FIG. 7 is a perspective view illustrating that the catheter fixing band illustrated in FIG. 6 is additionally equipped with a fixing ring.

FIG. 6 is a perspective view illustrating a catheter fixing band 300 according to another embodiment of the present disclosure. FIG. 7 is a perspective view illustrating that the catheter 3 of the catheter fixing band 300 illustrated in FIG. 6 is additionally equipped with a fixing ring 43.

A catheter fixing band 300 according to another embodiment of the present disclosure is the same as or similar to the catheter fixing band 100 described with reference to FIGS. 4 and 5, except that a catheter fixing portion for fixing the catheter 3 is added, so the same or similar configuration is not described here.

Referring to FIG. 6, the catheter fixing band 300 according to another embodiment of the present disclosure has sub-bands 41 and 42 at both ends in the longitudinal direction of a catheter hole 11 formed through a body 10. The sub-bands 41 and 42 fix the catheter 3 with respect to the body 10. In detail, the sub-bands 41 and 42 can fix the catheter 3 to the body 10 by covering the center of the catheter 3. By this configuration, the catheter 3 can be more firmly fixed to the body 10 and shaking the catheter 3 due to external force is reduced. Though not illustrated in the figures, Velcro tapes may be provided at ends and start portions of the sub-bands 41 and 42 to detachably stick back to the sub-bands 41 and 42 after winding around the catheter 3.

Meanwhile, the sub-bands 41 and 42 may be formed to cross each other. In other words, the first sub-band 41 and the second sub-band 42 are disposed across each other in the longitudinal direction of the catheter hole 11 such that the second sub-band 42 can cover the catheter 3 a little over the position where the first sub-band 41 covers the catheter 3.

Referring to FIG. 7, a fixing ring 43 having rings 43a at both sides is fitted at the center portion of the catheter 3. The sub-bands 41 and 42 can fix the catheter 3 by being inserted in the rings 43a formed at both sides of the fixing ring 43. A small difference in the left-right direction that may be generated when the catheter 3 is fixed directly by the sub-bands 41 and 42 can be reduced by the fixing ring 43.

Figure 8:
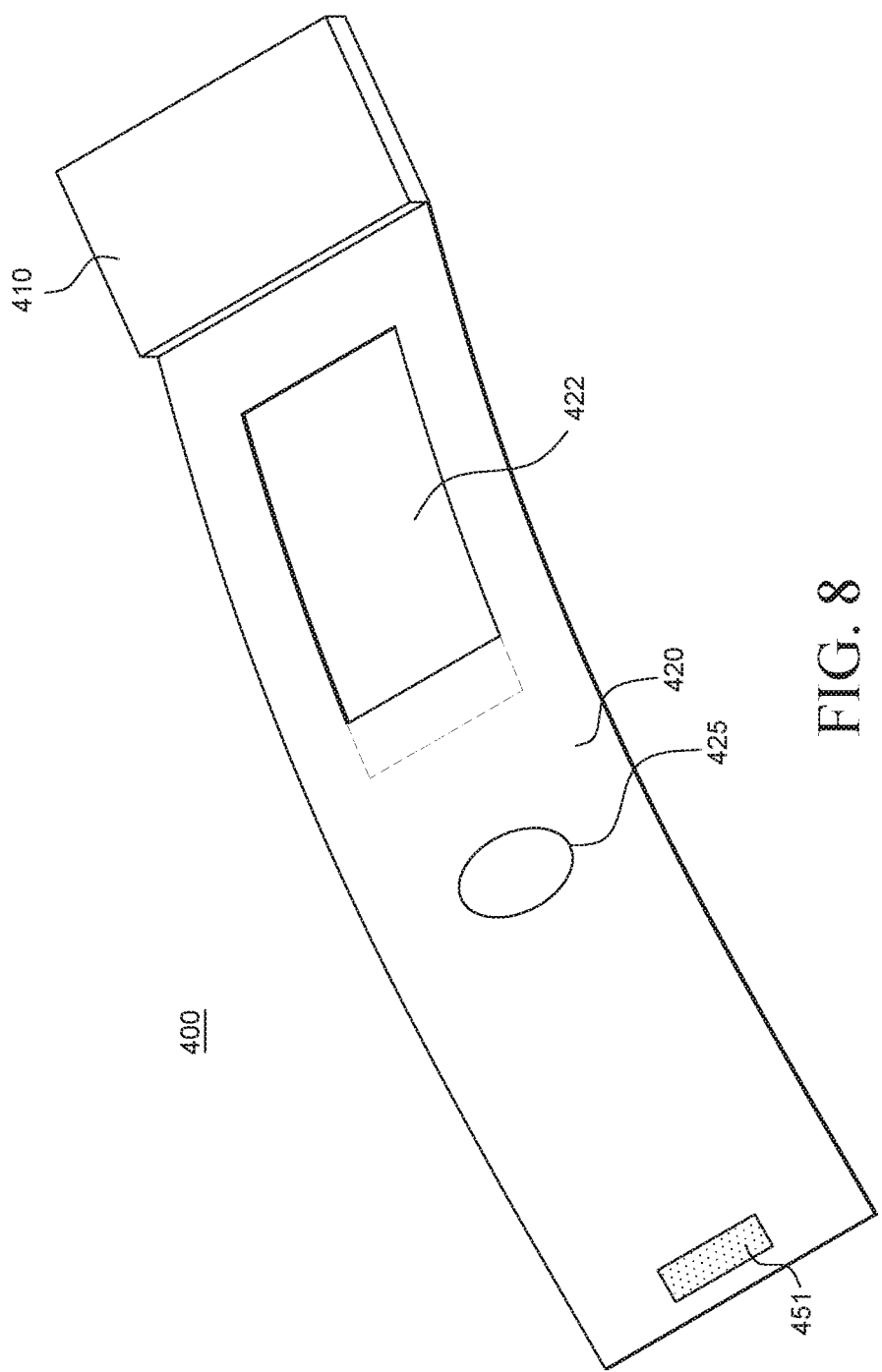
FIG. 8 is a perspective view illustrating a splint and a band part of a catheter fixing band according to another embodiment of the present disclosure.
Figure 9:
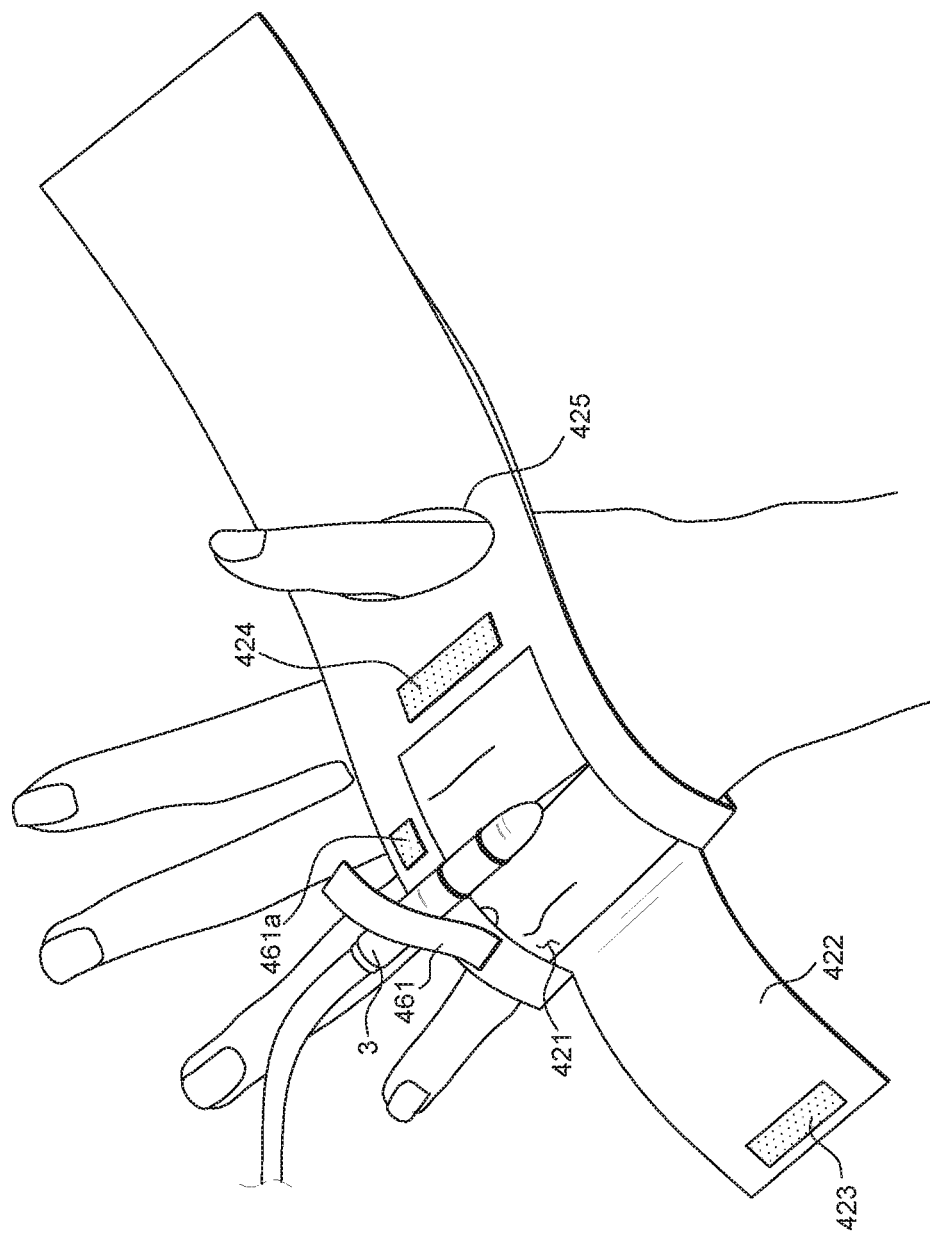
FIG. 9 is a perspective view illustrating a first step in a process of putting the catheter fixing band illustrated in FIG. 8 on a hand of a patient.
Figure 10:
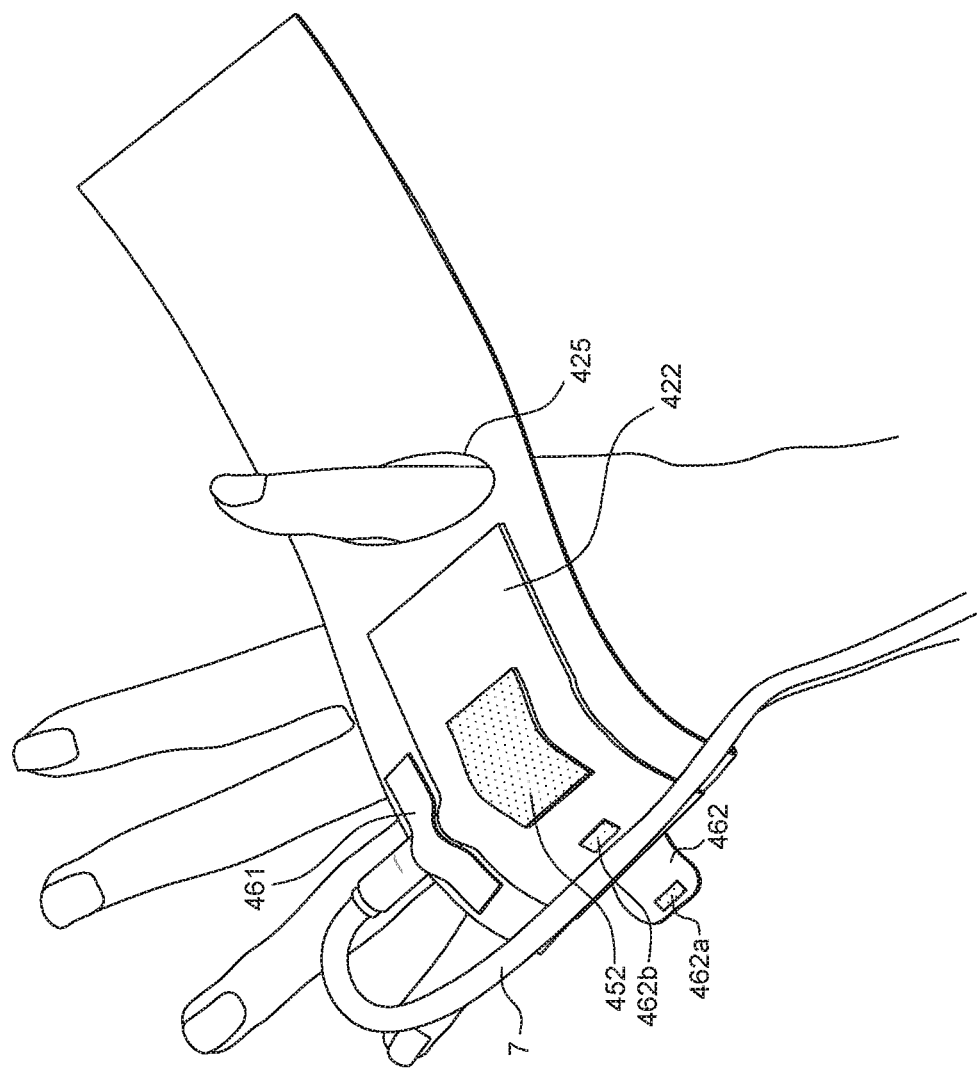
FIG. 10 is a perspective view illustrating a second step in the process of putting the catheter fixing band illustrated in FIG. 8 on a hand of a patient.
Figure 11:
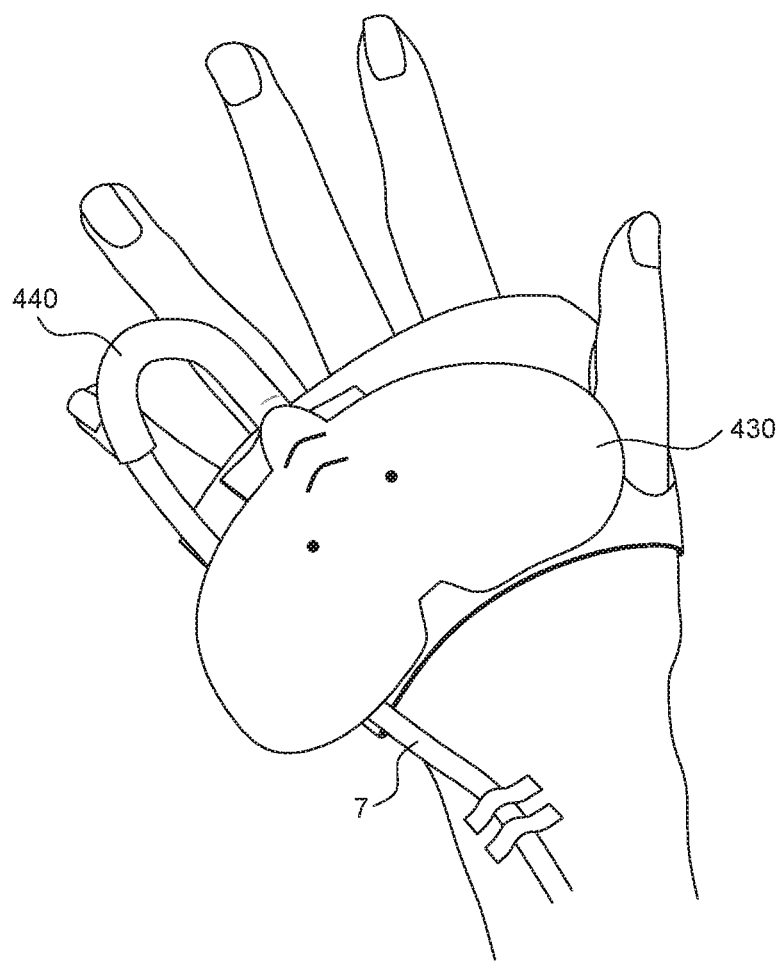
FIG. 11 is a perspective view illustrating that the catheter fixing band illustrated in FIG. 8 has been worn on a hand of a patient.

FIG. 8 is a perspective view illustrating a splint 410 and a body 420 of a catheter fixing band 400 according to another embodiment of the present disclosure. FIG. 9 is a perspective view illustrating a first step in a process of putting the catheter fixing band 400 illustrated in FIG. 8 on a hand of a patient. FIG. 10 is a perspective view illustrating a second step in a process of putting the catheter fixing band 400 illustrated in FIG. 8 on a hand of a patient. FIG. 11 is a perspective view illustrating that the catheter fixing band 400 illustrated in FIG. 8 has been worn on a hand of a patient.

The cover unit 430 of the catheter fixing band 400 according to another embodiment of the present disclosure is different in whether it is coupled to the body 10 or the body 420, as compared with the cover unit 20 described in reference FIG. 4, and other configurations are the same or similar, so refer to the above description for the details of the cover unit 430.

Referring to FIGS. 8 and 11, the catheter fixing band 400 according to another embodiment of the present disclosure includes a splint 410, a body 420, and a cover unit 430.

The splint 410 may be a hard wood member formed in the shape of a rectangle. The splint 410 is disposed at a portion where the catheter 3 is fixed when it is fixed to a wrist or an arm of a patient.

The body 420 has a coupling member that elongates to cover a portion of a body and then be coupled back to the body 420. The coupling member may be a Velcro tape. The body 420 may extend from a side of the splint 410. The body 420 winds around an arm or a leg of a patient and is then detachably attached to the splint 410 or the winding side of the body 420 to be fixed to a wrist or the arm of a patient. In other words, the splint 410 is positioned on a wrist or an arm of a patient and the body 420 winds a hand or the arm of the patient and is then coupled to the other side of the body 420 or the splint 410. As the body 420 is coupled after winding around a wrist or an arm of a patient, the body 420 and the splint 410 can be held on the hand or the arm of the patient. Further, the body 420 may have flexibility. Accordingly, if the body 420 is stretched to the maximum to wind around a hand or an arm of a patient, it can strongly wind around the arm or the hand by the elasticity.

The body 420 may have a catheter hole 421, a cover 422, and a catheter fixing member.

The catheter hole 421 is formed at a predetermined position of a side of the body 420 to pass the catheter 3 to be inserted in a patient. After the body 420 winds round a hand or an arm of a patient, the catheter 3 passes through the catheter hole 421.

The cover 422 covers the catheter hole 421. One end of the cover 422 is fixed to a side of the catheter hole 421.

Further, the other end is detachably attached to the body 420, covering the catheter hole 421. In other words, the cover 422 has one end fixed to the body 420 and the other end sticking to the body 420 by a Velcro tape. Further, the cover 422 corresponds to the catheter hole 421 and is larger than the catheter hole 421, so it can fully cover the catheter hole 421. Further, the cover 422 is longer than the catheter hole 421 to be coupled so that the other end can be coupled to the body 420 after covering the catheter hole 421. A cover Velcro tape 423 may be disposed at the other end of the cover 422 sticking to the body 422 by a Velcro tape.

The catheter fixing member is disposed on the body 420. The catheter fixing member fixes the tube 7 connected to the catheter 3 to the body or the body 420. The catheter fixing member may include a first fixing member 461 and a second fixing member 462. However, the number of the fixing members is not limited and one or more fixing members may be provided in the arrangement direction of the catheter 3 or the tube 7 connected to the catheter 3.

The first fixing member 461 is disposed at a side of the catheter hole 421. The first fixing member 461 covers the tube 7 and is detachably attached to the body 420 to fix the tube 7 coming out of the catheter hole 421 to the body 420. In detail, referring to FIGS. 9 and 10, the body 420 covers the back of a hand and the catheter hole 421 exposes a portion of the back of the hand. The catheter 3 is inserted into the back of the hand of the patient through the catheter hole 421. The catheter 3 is inserted in the back of the hand and the tube 7 comes out of the back of the hand. The first fixing member 461 covers the portion between both ends of the catheter 3 and is fixed to a first fixing member Velcro tape 461a on the body 420, thereby bringing the catheter 3 in close contact with the body 420.

The second fixing member 462 has one end that is fixed to the outer side of the cover 422 and the other end that sticks to the cover 422 by a Velcro tape. In detail, referring to FIGS. 10 and 11, the tube 7 connected to the catheter 3 fixed by the first fixing member 461 is bent in a U-shape and then returns to the body 420. In this case, the second fixing member 462 allows the tube 7 bending and extending to be fixed to the cover 422. In detail, a second fixing member Velcro tape 462a is disposed at one end of the second fixing member 462 and the second fixing member 462 covers the tube 7 with one end sticking to the cover outer Velcro tape 462b on the outer side of the cover 422. Accordingly, the second fixing member 462 can bring the tube 7 in close contact with the cover 422. The area exposed to the outside of the tube 7 can be reduced by the second fixing member 462. Further, since the tube 7 is in close contact with the body 420, when the tube 7 receives external force by touching an external object, the second fixing member 462 can absorb some of the external force. Accordingly, movement of the tube 7 can be reduced.

However, the first fixing member 461 and the second fixing member 462 are not fixed to the body 420, and the like only by Velcro tape, other coupling members that can detachably attach the first fixing member 461 and the second fixing member 462 to the body 420 may be used.

Further, the positions of the first fixing member 461 and the second fixing member 462 are not limited to the positions described above and may be changed in accordance with the arrangement direction of the catheter 3 and the tube 7 connected to the catheter 3. Further, the catheter fixing members such as the sub-bands 41 and 42 described with reference to FIGS. 6 and 7 may be disposed at the catheter hole 421 of the catheter fixing band 400 according to the present embodiment.

Meanwhile, the body 420 may be further elongated to be able to wind around a hand of a patient several times. In this case, the cover unit Velcro tape 452 may be disposed on the body 420. As the body 420 is further elongated and winds a hand of a patient several times, the second fixing member 462 can more stably fix the tube 7. Accordingly, even if friction or shock is applied to the tube 7 from the outside, the second fixing member 462 or the body 420 can absorb the shock, so a pain applied to a patient can be reduced.

Meanwhile, a finger hole 425 for passing at least some of the fingers of a patient may be formed in the body 420. In detail, when the catheter 3 is inserted into the back of a hand, the thumb passes through the finger hole 425. This is for allowing a hand to freely move and fingers to be naturally placed, because the thumb is different in direction from the other four fingers.

A cover unit 430 has a tube support portion 440 covering a tube 7 connected to a catheter 3 and extending in a U-shape from an end such that the tube 7 is bent in a U-shape. Further, the cover unit 430 is detachably attached to the body 420. The tube support portion 440 extending from the cover unit 430 can receive the tube 7 connected to the catheter 3 and bend the tube 7 in a U-shape.

However, the cover unit 430 according to another embodiment of the present disclosure, similar to the cover unit 430 described with reference to FIG. 4, may have an end fixed to the body 420 and the other end detachably attached to the body 420.

Meanwhile, the body 420 and the cover unit 430 may have Velcro tapes at their coupling portions to be detachably attached to each other. In detail, a cover unit Velcro tape 452 may be disposed on the outer side of the cover 422 over the body 420. Further, a corresponding Velcro tape may be disposed on the inner side of the cover unit 430. However, the body 420 and the cover unit 430 are not coupled only by Velcro tapes, but they may be coupled in various ways as long as they can be detachably attached to each other.

Meanwhile, unlike the figures, a cover unit without the tube support portion illustrated in FIGS. 1 to 3 may be used.

Figure 12:
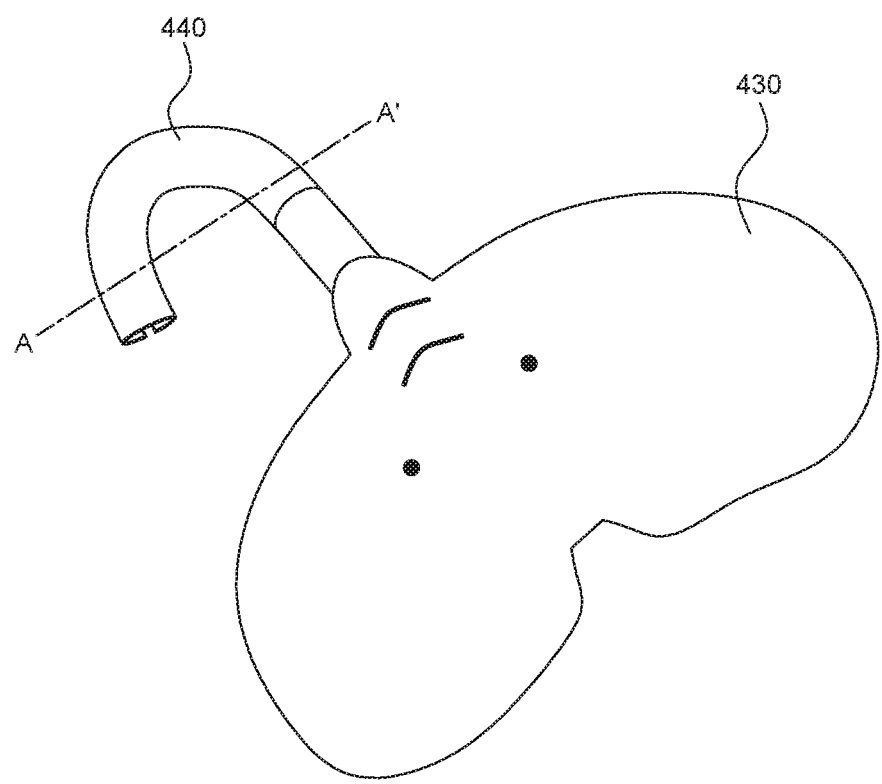
FIG. 12 is a perspective view illustrating a cover unit of the catheter fixing band illustrated in FIG. 11.

FIG. 12 is a perspective view illustrating the cover unit 430 of the catheter fixing band 400 illustrated in FIG. 11. FIG. 13 is a cross-sectional view illustrating the cross-section taken along line A-A' of the cover unit 430 illustrated in FIG. 12 and a process of inserting the tube 7 into the band cover unit 430.

The cover unit 430 in the present embodiment is different from the cover unit 430 illustrated in FIG. 4 only in that a side is fixed to the body, but the other configurations are the same, so the following description is applied to the cover unit 20 and the tube support portion 30 illustrated in FIG. 4.

Referring to FIG. 12, a tube support portion 440 extends in a U-shape from an end of the cover unit 430.

The cover unit 430 may be formed in any shapes as long as it can cover the band part 420. The cover unit 430 is provided to cover the band part 420 and suppress the catheter 3 or the tube 7 connected the catheter 3 from being exposed to the outside, so the shape is not limited as long as the cover unit 430 can cover the band part 420.

Various pictures may be provided for the cover unit 430 to reduce mental burden and anxiety. For example, as illustrated in the figures, an elephant may be drawn, and various animals such as a tiger, lion, bear, elephant, dog, rabbit, penguin, dinosaur, and hippopotamus may be drawn. In this case, a picture may be provided on the U-shaped tube support portion 440 too. For example, the tube support portion 440 may be the nose of an elephant or may be the tail of a tiger or a lion.

Further, the cover unit 430 may have a pattern as fashion. Further, it may be made of a material that is appropriately hard and permeated with ink to leave characters.

Referring to FIG. 13, the tube support portion 440 has a cover semicircle 441 and a grip curved surface 442.

The cover semicircle 441 makes the upper semicircle of the tube support portion 440. The cover semicircle 441 is formed in a semicircular shape and made of a rigid material not to be moved by external force. The cover semicircle 441 protects the tube 7 from external force, when the tube 7 is inserted therein.

The grip curved surface 442 extends around the cover semicircle 441. Further, the grip curved surface 442 is made of an elastic material. The grip curved surface 442 can support the tube 7 so that the tube 7 is inserted and seated in the cover semicircle 441.

In detail, referring to FIG. 13, (a) is a cross-section of the tube support portion 440 before the tube 7 is inserted, (b) is a cross-section of the tube support portion 440 when the tube 7 is being inserted, and (c) is a cross-section after the tube 7 is inserted in the tube support portion 440.

Referring to (a) first, the grip curved surface 442 extends around the cover semicircle 441. The grip curved surface 442 may extend around the cover semicircle 441, but as illustrated in the figures, it is preferably formed at an angle inward further than the circle made by the cover semicircle 441. This is for more strongly supporting the tube 7 to the cover semicircle 441 when the tube 7 is inserted in the tube support portion 440.

Next, referring to (b), the tube 7 is being inserted in between the grip curved surfaces 442. When the tube 7 is inserted in between the grip curved surfaces 442, the grip curved surfaces 442 are opened to both sides. Further, the grip curved surfaces 442 apply elastic force (or return force) in the direction of pressing the tube 7. Accordingly, when the tube 7 is inserted at a predetermined depth, the tube 7 is pressed by the grip curved surfaces 442, so the tube 7 is easily inserted into the cover semicircle 441.

Next, referring to (c), the tube 7 has been inserted in the tube support portion 440. Compared with (a), it can be seen that the grip curved surface 442 makes a circle the same as that made by the cover semicircle 441. That is, the grip curved surfaces 442 are pushed outward by the tube 7 further than the position in (a). Since the grip curved surfaces 442 has elasticity, a return force as large as the pushed distance is generated and pushes the tube 7.

FIGS. 14a to 14e are plan views illustrating steps of putting a catheter fixing band according to another embodiment of the present invention on a hand of a patient.

Referring to FIGS. 14a to 14e, a catheter fixing band 500 includes a body 510, velcro tape portions 520 and 530 and a cover unit 540.

The body 510 may be a piece of rectangular cloth or fabric. An attachment side may be formed on the side of the body 510 that is brought in contact with the patient to be easily attached to the body of the patient.

The body 510 has a finger hole 512, a fixing member for fixing a catheter to the body 510, and a catheter hole 518.

The finger hole 512 is a part in which patient's fingers except for the thumb are inserted with the body 510 on the back of a patient's hand. The finger hole 512 is elongated in the width direction of the body 510 to insert fingers. The body 510 is divided into a portion facing the back of a hand and a portion folded to the palm. Referring to FIG. 14b, fingers are inserted in the finger hole 512 and the upper portion of the body 510 is folded. However, if the catheter fixing band 500 is not on the back of a hand, fingers may not be inserted into the finger hole 512. In this case, it is possible to fix the body 510 to the body of a patient using the velcro tape portions 520 and 530.

The fixing member may be made of a velcro tape to be able to fix a catheter to the body 510. The fixing member may be disposed at the lower end of the finger hole 512. Meanwhile, the fixing member may include a first fixing member 514 and a second fixing member 516. The first fixing member 514 can fix a catheter at a predetermined position around the center portion of the body 510 so that the catheter can be inserted into a patient through the catheter hole 518. The second fixing member 516 fixes a tube connected to a catheter at a predetermined position.

The catheter hole 518 may be formed by cutting off a portion of the body 510 under the fixing member. The catheter hole 518 provides a space through which a catheter can be inserted into a patient.

The velcro tape portions are disposed at the upper and lower ends of the body 510. Since the velcro tape portions are elongated, they can fix the body 510 on the body of a patient by surrounding the body of the patient.

The velcro tape portions 520 and 530 are a first velcro tape portion 520 disposed close to the finger hole 512 and a second velcro tape portion 530 disposed opposite to the first velcro tape portion 520. The first velcro tape portion 520 can be wound around the body of a patient toward the fixing member when the upper end of the body 510 is folded, as described above. The first velcro tape portion 520 may have a velcro tape on both sides. This is for fixing the body 510 around the body of a patient when the first velcro tape portion 520 is folded or not. The second velcro tape portion 530 is disposed at the end portion of the body 510 opposite to the first velcro tape portion 520. Since the second velcro tape portion 530 is also elongated, it can fix the body 510 on the body of a patient.

Meanwhile, though not illustrated in the figures, the body 510 may be elongated like the bodies 510 and 420 illustrated in FIG. 8. When the body 510 is elongated as described above, it can also be wound around the body of a patient. When the body 510 is also wound around the body of a patient with a catheter fixed, the catheter can be more firmly fixed in the body of the patient.

The cover unit 530 is disposed close to the second velcro tape portion 530. The cover unit 540 is turned over the body 510 after a catheter is fixed, so an integrated concept is achieved in relation to inward/outward flow of fluid in the catheter. Velcro tapes 544 may be disposed on the inner side of the cover unit 540 to be attached/detached to/from the body 510. Further, the body 510 may be made of a material where a velcro tape can be easily attached/detached.

The entire shape of the cover unit 540 may be an elephant. Further, the portion connected to a catheter when the cover unit 540 is attached to the body 510 may be a nose 542 of the elephant. The nose 542 may bend like the tube support portion illustrated in FIG. 11. Further, the nose 542 may have a grip curved surface, as illustrated in FIG. 13.

Order of putting the catheter fixing band 500 is described hereafter with reference to FIGS. 14a to 14e.

This embodiment exemplifies that the catheter fixing band 500 is put on the back of a hand. However, the catheter fixing band 500 may be put on an arm or a calf.

Figure 14A:
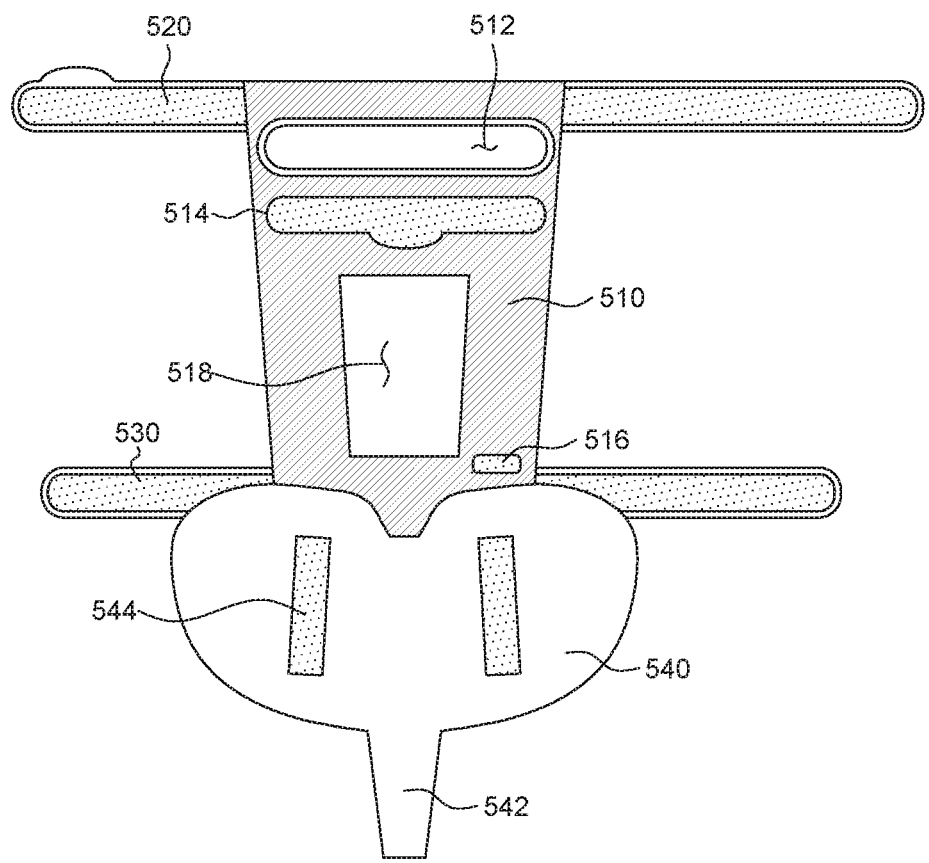
FIGS. 14a to 14e are plan views illustrating steps of putting a catheter fixing band according to another embodiment of the present invention on a hand of a patient.
Figure 14B:
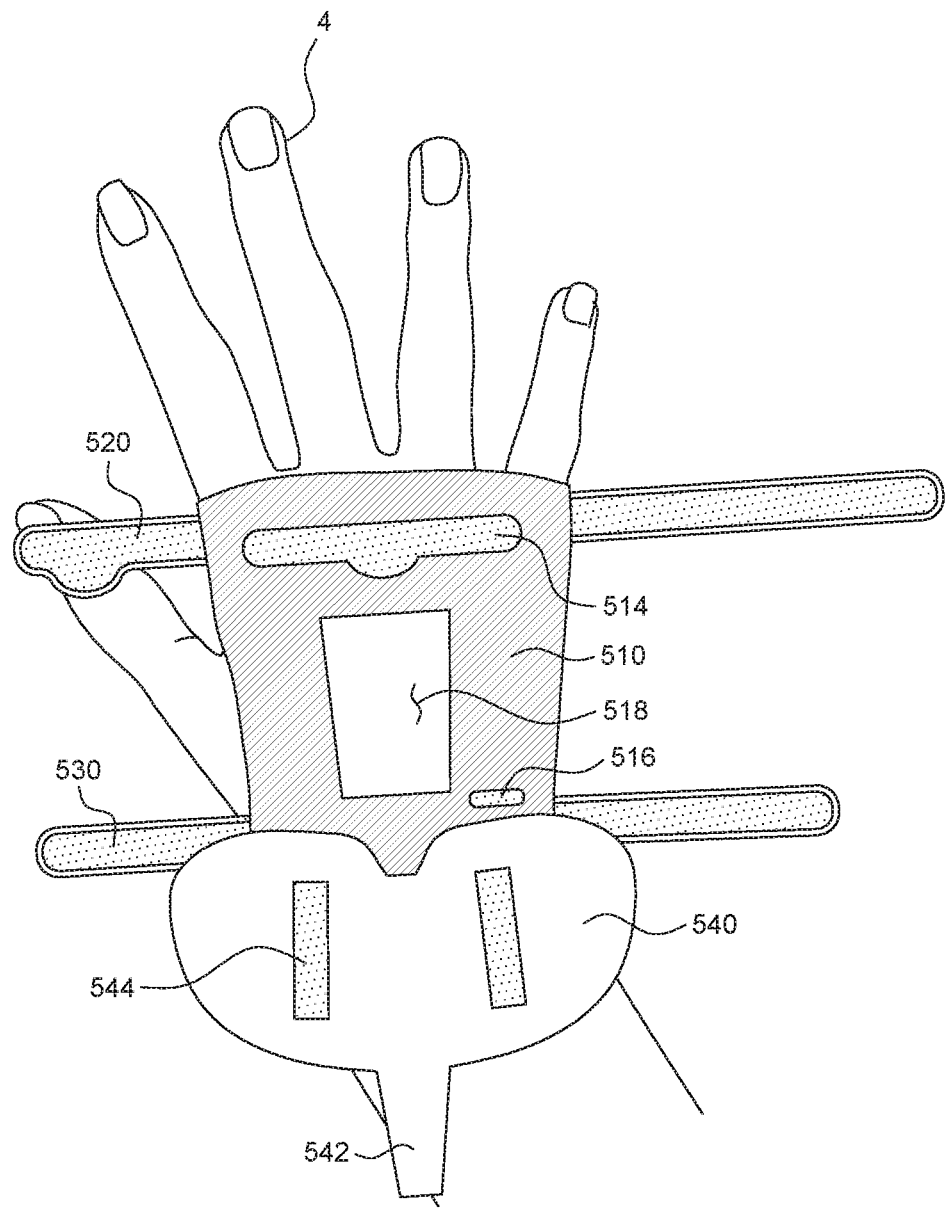

Referring to FIGS. 14a and 14b, fingers of a patient may be inserted in the finger hole 512 of the body 510 with the first velcro tape portion 520 bending inside the palm. The body 510 covers the back of the patient's hand. The back of the hand is exposed through the catheter hole 518.

Figure 14C:
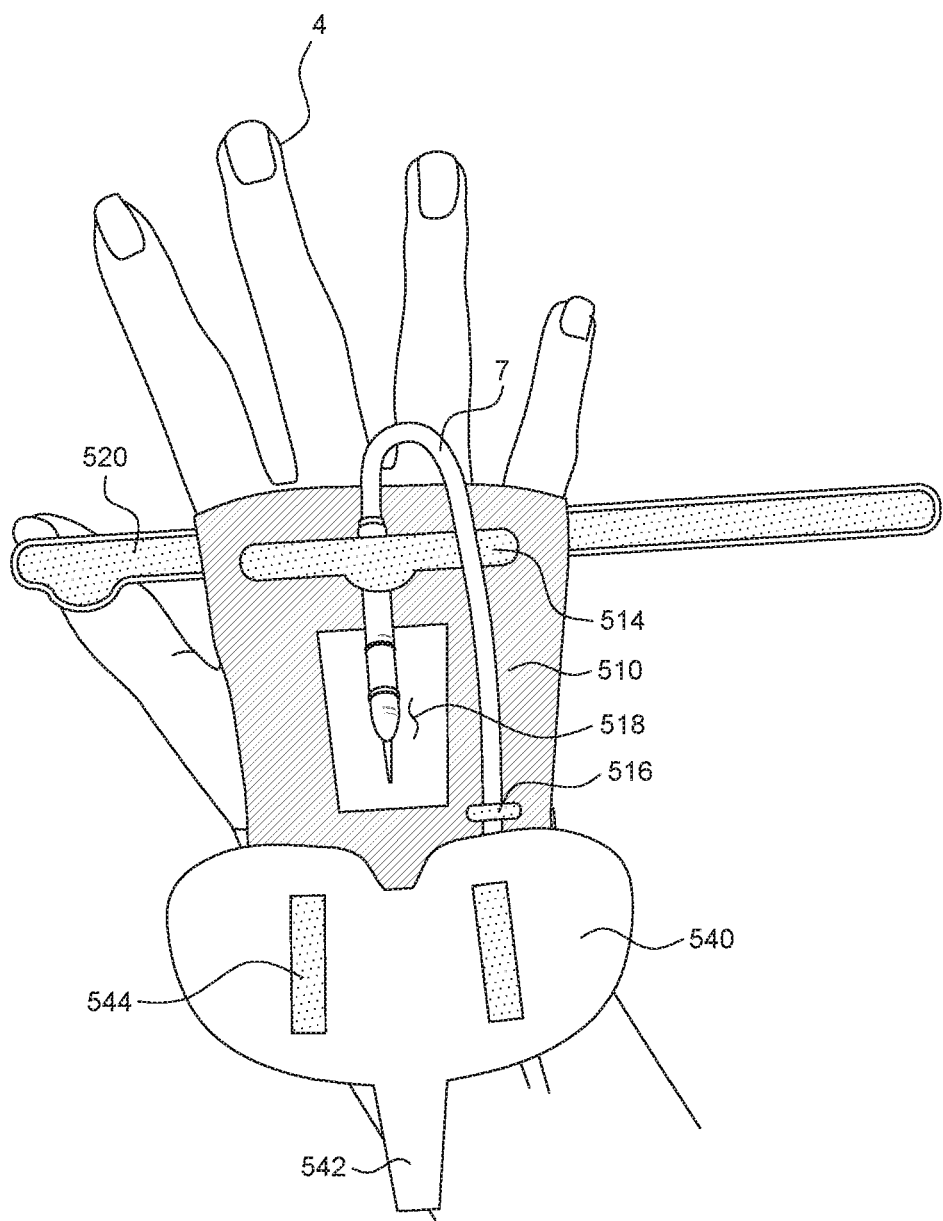

Referring to FIG. 14c, the second velcro tape portion 530 is wound around the wrist of the patient. Accordingly, the body 510 is brought in close contact with the back of the patient's hand. The fixing member fixes a catheter so that the catheter can be fixed after being inserted in the back of the hand through the catheter hole 518. The first fixing member 514 fixes the catheter to the body 510 and the second fixing member 516 fixes a tube connected to the catheter at a predetermined position on the body 510.

Figure 14D:
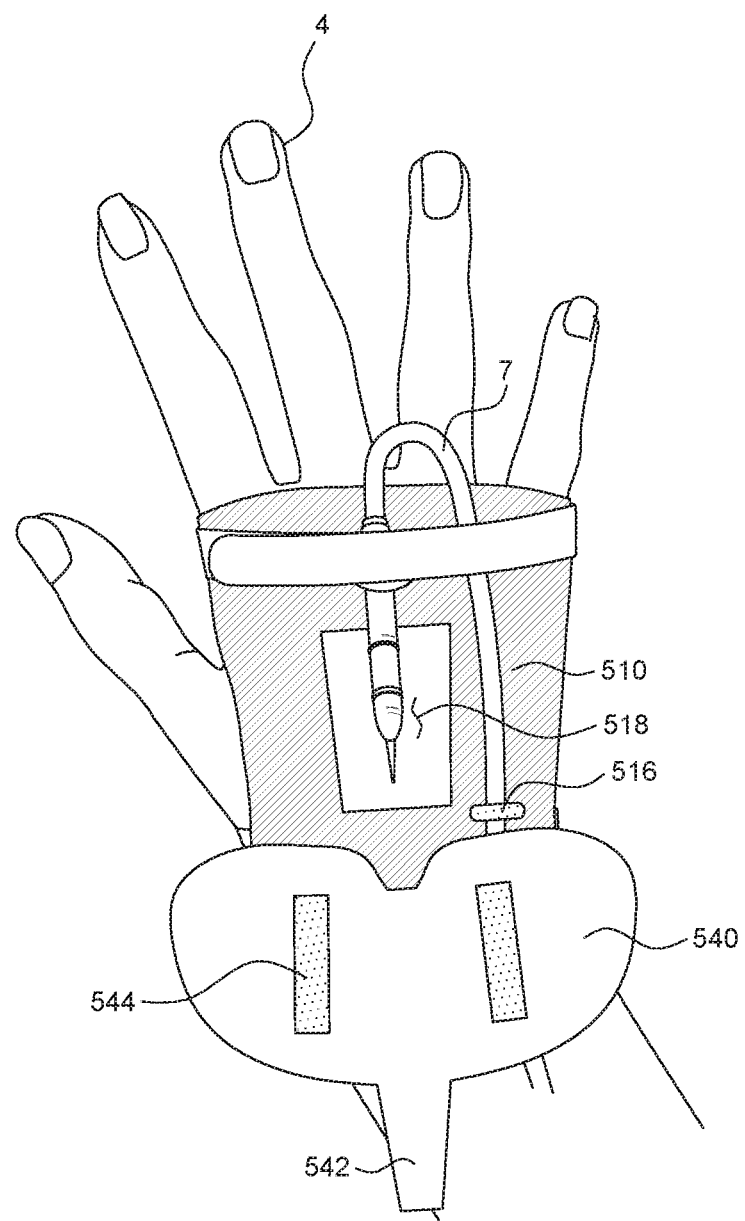

Referring to FIG. 14d, the first velcro tape portion 520 is wound up and attached to the first fixing member 514. The outer side of the first fixing member 514 may be fixed by a velcro tape.

Figure 14E:
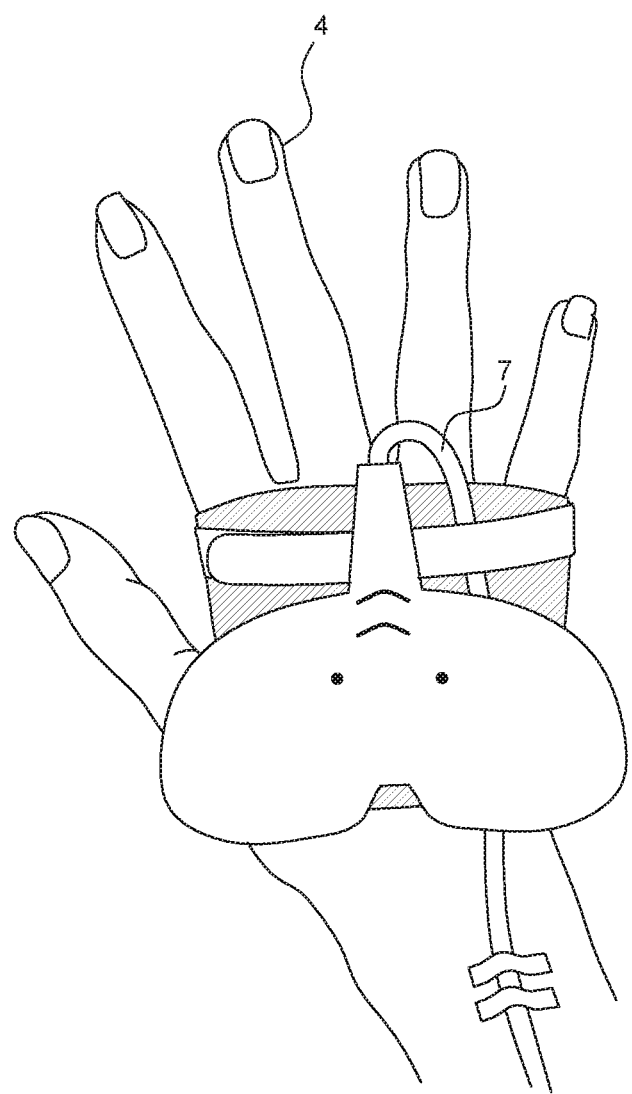

Referring to FIG. 14e, the cover unit 540 is attached to the body 510 over the catheter. The nose 542 partially cover the tube 7 connected to the catheter. Accordingly, the nose 542 looks like be integrated with a portion of the tube. Further, an integrated concept like the tube 7 comes out of the nose of an elephant is achieved.

FIGS. 15a to 15d are plan views illustrating steps of putting a catheter fixing band 600 according to another embodiment of the present invention on a hand of a patient.

Referring to FIGS. 15a to 15d, a catheter fixing band 600 includes a body 610, and a cover unit 630.

A side of the body 610 may be an attachment side. The attachment side of the body 610 may be attached to the back of a patient's hand. That is, the body 610 may have an attachment side that is directly attached to the skin of a patient.

In this case, although it is exemplified that the body 610 is supposed to be attached to the back of a patient's hand, it may be attached to various parts such as an arm, a leg, and a body. A catheter hole 618 may be formed through the body 610.

The body 610 may further have a fixing member 620. The fixing member 620 is connected to a side of the body 610 and can be turned. The fixing member 620 may be made of a velcro tape, but may be made of any material as long as it can be attached to other side, not the attachment layer of the body 610. The fixing member 620 includes a first fixing member 621 that can fix a catheter 3 and a second fixing member 622 that can fix a tube 7 extending from the catheter 3.

Figure 15A:
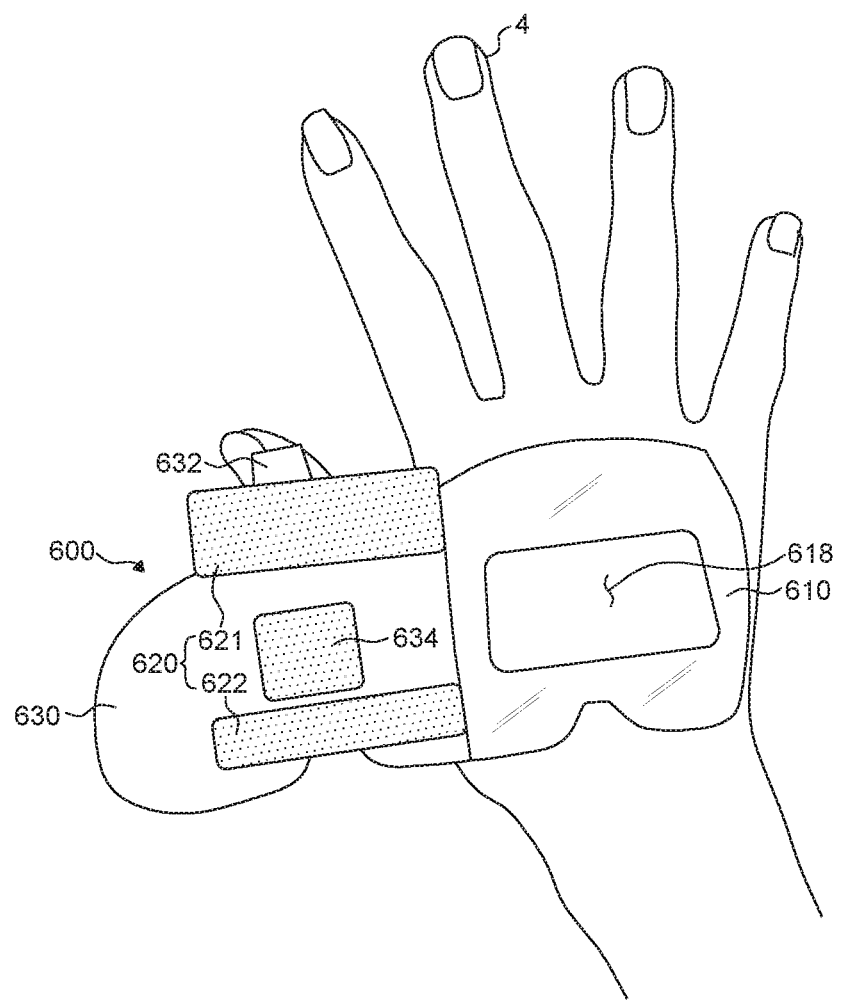
FIGS. 15a to 15d are plan views illustrating steps of putting a catheter fixing band according to another embodiment of the present invention on a hand of a patient.
Figure 15B:
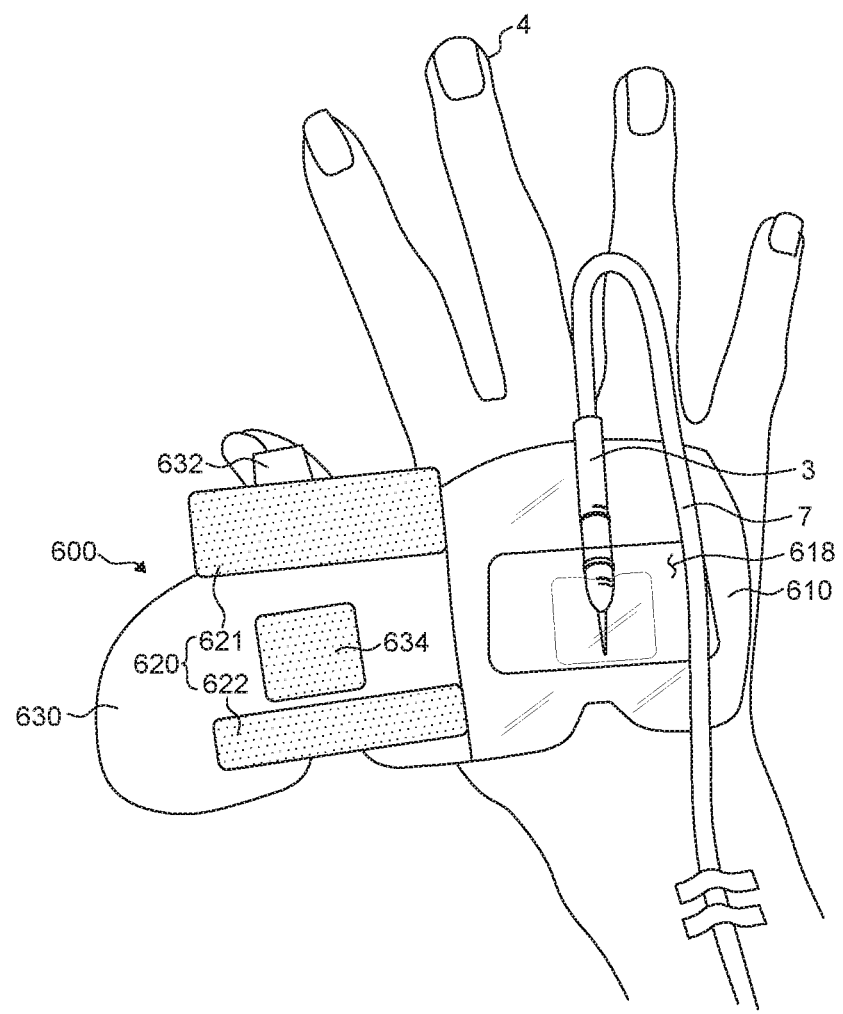
Figure 15C:
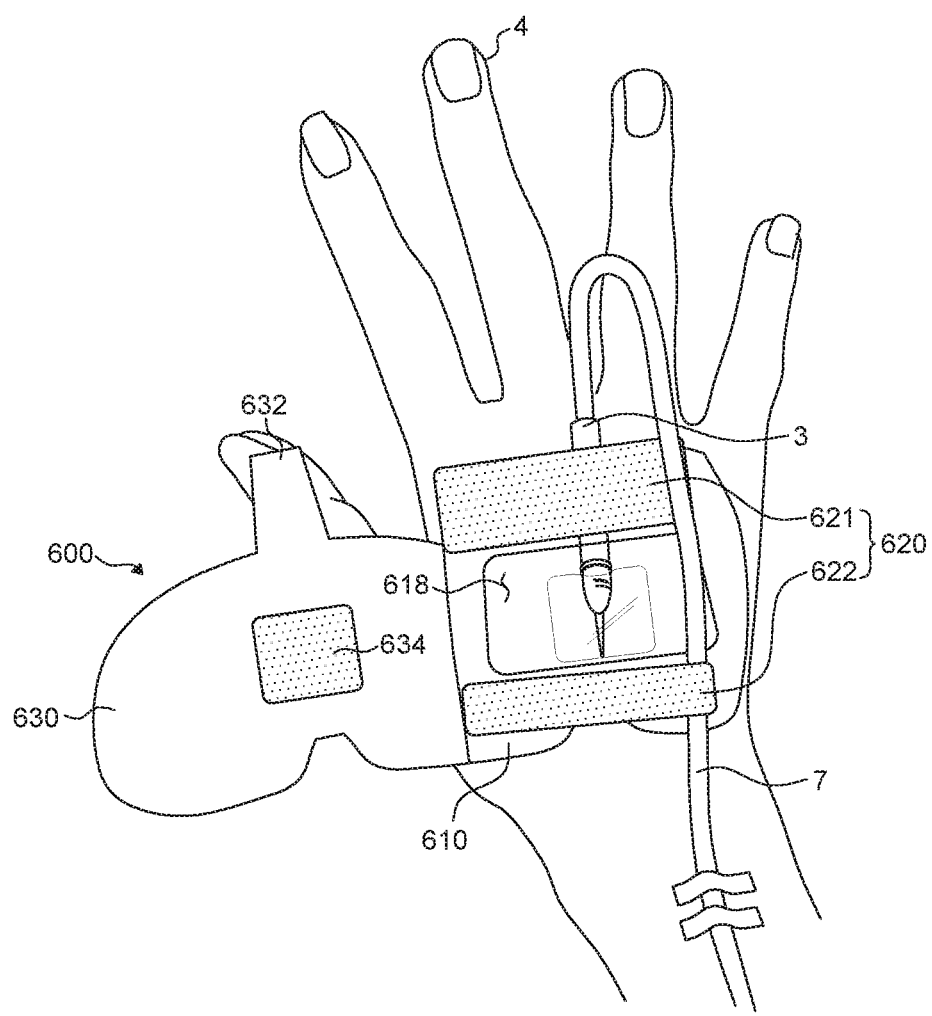

Referring to FIG. 15c, the catheter 3 is fixed to the body 610 by the first fixing member 621 and inserted in the body of a patient through the catheter hole 619. The tube 7 extending from the catheter 3 is fixed to the body 610 by the second fixing member 622.

The cover unit 630 can be turned at a side of the body 610. The cover unit 630 is positioned close to the fixing member 620 of the body 610.

The cover unit 630 can be turned over the body 610 after the catheter 3 is fixed to the body 610. A protrusion 631 may be formed at the middle portion of the cover unit 630. The protrusion 632 may be formed at the cover unit 630 to cover the catheter 3 and the tube after the cover unit 630 covers the body 610. Further, though not illustrated in FIGS. 15a to 15d, a tube fixing member may be formed inside the protrusion 632 of the cover unit 630. A portion of the tube 7 can be inserted in the protrusion 632 by the tube fixing member. Accordingly, the cover unit 630 cannot be easily separated from the catheter 3.

The cover unit 630 may further have an attachment member such as a velcro tape to be attached to the body 610. The attachment member may be the attachment members described above.

A covering portion 634 that can cover the portion of the catheter 3 inserted in the body of a patient may be disposed at the center portion on the inner side of the cover unit 630. The covering portion 634 can further sanitize the catheter fixing band 600 by covering the needle of the catheter 3 inserted in the body. Further, the cover unit 630 is not directly attached to the portion where the catheter 3 is inserted, so a pain due to the cover unit 630 attached to the catheter 3 can be reduced.

Order of putting the catheter fixing band 600 is described hereafter with reference to FIGS. 15a to 15d.

Referring to FIG. 15a first, the body 610 is attached to the back of a patient's hand. In this case, a user removes a separation paper on the attachment side and attach the body 610 to the back of the patient's hand such that the catheter hole 618 is positioned on a desired portion. In this case, the first fixing member 621 and the second fixing member 622 can be pressed in one direction not to be attached to the body 610.

Referring to FIG. 15b, the catheter 3 may be disposed at the upper end of the body 610. The end of the catheter 3 is inserted in the back of the patient's hand through the catheter hole 618. A band may be attached to the end of the catheter 3 to fix the catheter 3 after it is inserted. Meanwhile, the tube 7 connected to the catheter 3 may be bent at the end of the catheter 3 and placed under the body 610. This is for fixing not only the catheter 3, but the tube 7 under the body 610 using the fixing member 620.

Referring to FIG. 15c, the first fixing member 621 is fixed to the body 610 over the catheter 3. Accordingly, the catheter 3 is attached to the body 610 by the first fixing member 621. Further, the second fixing member 622 is attached to the body 610 over the tube 7. The tube 7 is fixed to the body 610 by the second fixing member 622. As described above, since the tube 7 connected to the catheter 3 is bent and the fixed to the body 610, the portion of the tube 7 close to the catheter 3 can be bent in a U-shape and fixed to the body 610. Since the tube 7 is bent in a U-shape and fixed to the body 610, even if an external force is applied to the tube 7, the force is less transmitted to the patient through the catheter 3.

Figure 15D:
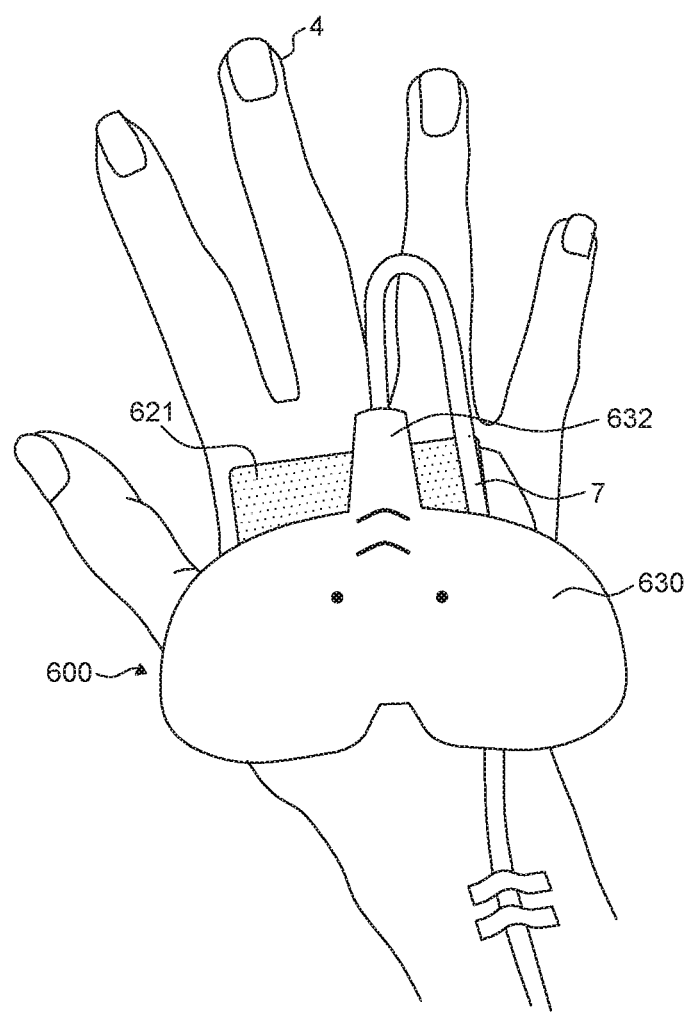

Referring to FIG. 15d, the cover unit 630 is turned over the body 610. The cover unit 630 is attached to a side of the body 610 and can be turned. After the catheter 3 is inserted into the back of a patient's hand and the catheter 3 and the tube 7 are fixed to the body 610, the cover unit 630 can be turned and fixed over the body 610. An attachment member such as a velcro tape that can be attached/detached to/from the body 610 may be disposed on the inner side of the cover unit 630.

As the cover unit 630 covers the body 610, the tube 7 can be positioned at the end of the protrusion 632 of the cover unit 630. Accordingly, a shape in which the protrusion 632 of the cover unit 630 is integrated with the tube 7 can be achieved. In detail, the cover unit 630 may be an elephant shape and the protrusion 632 may be the nose of the elephant shape. Further, since the tube 7 looks like extend from the protrusion 632, fluid looks like come out or flow into the nose of the elephant. The patient can be mentally stabilized because the animal shape of the cover unit 630 and the fluid flowing through the tube 7 make an integrated concept.

Meanwhile, the catheter fixing band 600 can be attached to any part of the body by the attachment side of the body 610, so it can be easily attached to any part of the patient's body.

Although the exemplary embodiments of the present disclosure have been described with reference to the accompanying drawings, those skilled in the art would understand that various modifications and alterations may be made without departing from the technical idea or essential features of the present disclosure. Therefore, it should be understood that the exemplary embodiments are not limiting but illustrative in all aspects.

What is claimed is:

1. A catheter fixing band comprising:
a body detachably fixed to a human body and having a catheter hole open to expose a portion of the human body; and
a cover unit detachably attached to the body to open or close the catheter hole,
wherein the cover unit includes a fixing member fixing a catheter to a predetermined position of the cover unit, and
wherein the cover unit has an animal shape bringing up an image of an animal, and
the fixing member is configured to fix the catheter or a tube connected to the catheter to the cover unit by covering the catheter or the tube, and
wherein the tube connected to the catheter forms at least a portion of the animal shape of the cover unit or the tube connected to the catheter is directly connected to a portion of the animal shape of the cover unit to form an integral shape with the animal shape.

* * * * *